US009527877B2

(12) United States Patent
Skowerski et al.

(10) Patent No.: US 9,527,877 B2
(45) Date of Patent: *Dec. 27, 2016

(54) METAL COMPLEXES, THEIR APPLICATION AND METHODS OF CARRYING OUT OF METATHESIS REACTION

(71) Applicant: Apeiron Synthesis S.A., Wroclaw (PL)

(72) Inventors: Krzysztof Skowerski, Jablonowo Pomorski (PL); Michal Bieniek, Wroclaw (PL)

(73) Assignee: APEIRON SYNTHESIS S.A., Wroclaw (PL)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,287

(22) Filed: Dec. 12, 2014

(65) Prior Publication Data

US 2015/0126744 A1   May 7, 2015

Related U.S. Application Data

(63) Continuation of application No. 13/920,230, filed on Jun. 18, 2013, now Pat. No. 8,933,242.

(60) Provisional application No. 61/666,009, filed on Jun. 29, 2012.

(51) Int. Cl.
| | | |
|---|---|---|
| *C07F 15/00* | (2006.01) | |
| *B01J 31/22* | (2006.01) | |
| *C07C 6/06* | (2006.01) | |
| *C07C 7/10* | (2006.01) | |
| *C07C 7/12* | (2006.01) | |
| *C07C 67/475* | (2006.01) | |
| *C07D 207/46* | (2006.01) | |
| *C07D 307/28* | (2006.01) | |
| *C07F 7/18* | (2006.01) | |
| *C07F 7/20* | (2006.01) | |

(52) U.S. Cl.
CPC ........ *C07F 15/0046* (2013.01); *B01J 31/2295* (2013.01); *C07C 6/06* (2013.01); *C07C 7/10* (2013.01); *C07C 7/12* (2013.01); *C07C 67/475* (2013.01); *C07D 207/46* (2013.01); *C07D 307/28* (2013.01); *C07F 7/1892* (2013.01); *C07F 7/20* (2013.01); *C07C 2101/08* (2013.01); *C07C 2531/22* (2013.01)

(58) Field of Classification Search
CPC .................................................. C07F 15/0046
See application file for complete search history.

(56) References Cited

U.S. PATENT DOCUMENTS

| 6,867,303 | B2 | 3/2005 | Grela |
|---|---|---|---|
| 6,921,735 | B2 | 7/2005 | Hoveyda |
| 7,687,635 | B2 | 3/2010 | Verpoort |
| 7,723,255 | B2 | 5/2010 | Hoveyda |
| 7,820,843 | B2 | 10/2010 | Pederson et al. |
| 7,939,668 | B2 | 5/2011 | Puentener |
| 8,008,224 | B2 | 8/2011 | Berlin |
| 8,063,232 | B2 | 11/2011 | Hagadorn et al. |
| 8,067,610 | B2 | 11/2011 | Schrodi |
| 8,288,534 | B2 | 10/2012 | Doppiu et al. |
| 8,288,558 | B2 | 10/2012 | Arlt et al. |
| 8,309,737 | B2 | 11/2012 | Parsy et al. |
| 2009/0275714 | A1* | 11/2009 | Puentener et al. ............ 526/171 |
| 2010/0036116 | A1 | 2/2010 | Scalone et al. |
| 2011/0306815 | A1 | 12/2011 | Hagadorn |
| 2012/0101279 | A1 | 4/2012 | Winde |

FOREIGN PATENT DOCUMENTS

| CN | 102476060 | 5/2012 |
|---|---|---|
| CN | 102476061 | 5/2012 |
| FR | 2934178 | 1/2010 |
| JP | 2011246624 | 12/2011 |
| PL | 199428 | 9/2008 |
| WO | 03044060 | 5/2003 |
| WO | 2005053843 | 6/2005 |
| WO | 2007054483 | 5/2007 |
| WO | 2008065187 | 6/2008 |
| WO | 2009126831 | 10/2009 |
| WO | 2010/015545 A1 | 2/2010 |
| WO | 2010090976 | 8/2010 |
| WO | 2010127964 | 11/2010 |
| WO | WO2010127964 | 11/2010 |
| WO | 2011023674 | 3/2011 |
| WO | 2011091980 | 4/2011 |
| WO | 2011056874 | 5/2011 |
| WO | 2011056881 | 5/2011 |
| WO | 2011079439 | 7/2011 |
| WO | 2011079799 | 7/2011 |
| WO | 2011119778 | 9/2011 |
| WO | 2012032131 | 3/2012 |
| WO | 2012097379 | 7/2012 |

OTHER PUBLICATIONS

Chatterjee, 2001, Synlett, p. 1034-1037.*
ISR and Written Opinion for PCT/EP2013/062435, mailed Oct. 4, 2013, international filing date Jun. 14, 2013.
Rafal Gawin et al:, A Dormant Ruthenium Catalyst Bearing a Chelating Carboxylate Ligand: In Situ Activation and Application in Metathesis Reactions. Angewandte Chemi E International Edition. 46(38):7206-7209, Sep. 24, 2007.
Cambridge MedChem Consulting:"Bioisosteric replacements" ••Jun. 18, 2012. Saved May 22, 2015, from URL: www.cambridgemedchemconsulting.com/resources/bioisoteres/acid_bioisosteres.html.
Skowerski, Krzysztof, et al., "Efficient, durable, and reusable olefin metathesis catalysts with high affinity to silica gel," Elsevier Ltd., Tetrahedron 69 (2013), 7438-7475; Jun. 2013; Journal Homepage: www.elsevier.com/locate/tet.
Skowerski, K., et al., Apeiron Synthesis A.A. webpage, http://apeiron-catalysts.com/products/greencat-catalyst-for-application-in-green-solvents.

* cited by examiner

*Primary Examiner* — Michael Barker
*Assistant Examiner* — Karen Cheng
(74) *Attorney, Agent, or Firm* — K&L Gates LLP; Brent A. Johnson; Louis C. Cullman

(57) ABSTRACT

This disclosure relates to new metal complexes, such as compounds of Formula 1, and their application in olefin or alkyne metathesis and to methods of carrying out olefin metathesis reactions.

18 Claims, No Drawings

METAL COMPLEXES, THEIR APPLICATION AND METHODS OF CARRYING OUT OF METATHESIS REACTION

CROSS-REFERENCE TO RELATED APPLICATIONS

This application is a continuation of U.S. application Ser. No. 13/920,230, filed Jun. 18, 2013, which claims the benefit of U.S. Provisional Patent Application No. 61/666,009, filed Jun. 29, 2012, which is incorporated by reference herein in its entirety.

BACKGROUND

Great progress has been made in developing of catalysts for olefin metathesis reactions (including stable and active catalysts, such as formula A and B). It allows application of metathesis to synthesis a large number of compounds.

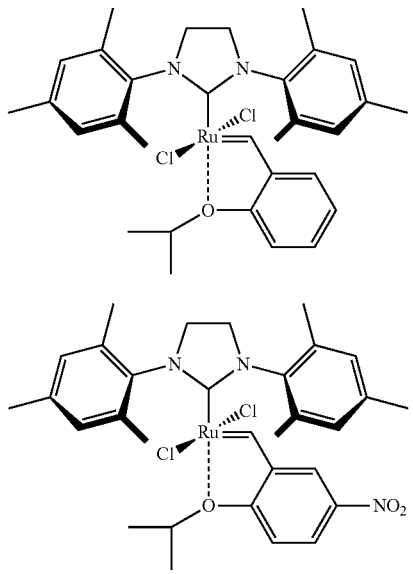

Removing heavy-metal containing impurities from reaction products may be important for the introduction of olefin metathesis in pharmaceutical industry. The development of an efficient, economical and practical method to remove metal by-products may help to further application of metathesis methodology.

Several scavengers have been proposed to remove residual Ru from reaction mixtures or from crude products. There is no universally attractive method so far. The protocols mentioned above were used when classical, non-tagged catalysts were applied.

In order to develop new processes for the removal of ruthenium from reaction products, a few immobilized catalysts which contain an onium group have been synthesized. It was shown that a simple purification step resulted in low levels of residual Ru impurities in the crude products. However Ru levels may still be too high for pharmaceutical application.

There is only limited number of complexes bearing quaternary ammonium groups known in the literature. This may be due to complicated synthesis and purification of such a complex. Alternatively, polar, uncharged complexes, with high affinity to adsorbents can be applied to facilitate residual Ru removal. For example complexC with high affinity to silica gel was synthesized. Application of C in metathesis resulted in products with significantly reduced residual ruthenium after a simple purification step.

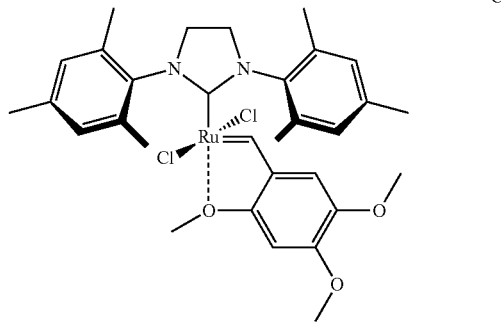

However, the results obtained with C were still far from the requirements of the pharmaceutical industry (residual Ru in the product ranged from 83 to 420 ppm).

Complexes bearing amido groups such as D and E were synthesized as well.

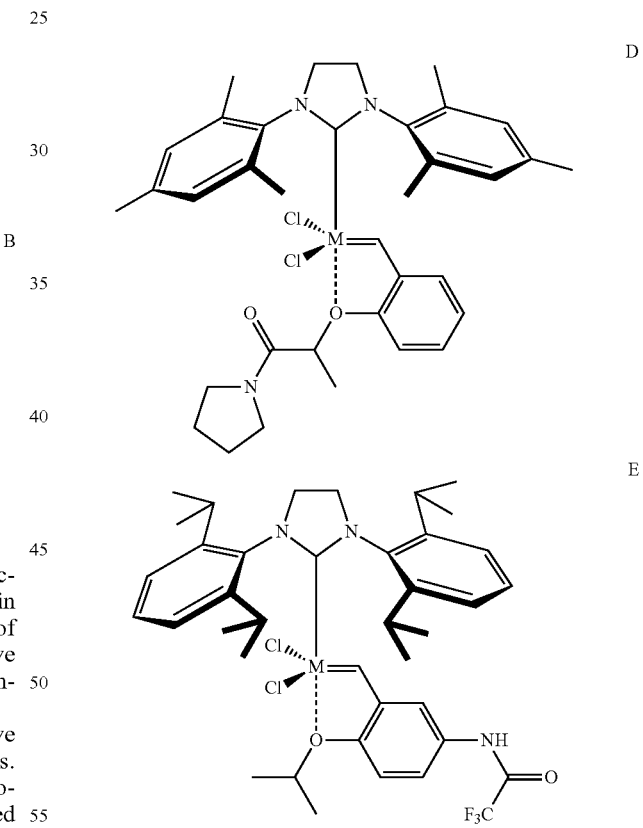

However, in case of reactions catalysed by D or E the possibility of residual Ru removal by simple filtration of reaction mixture through a small amount of adsorbent was not demonstrated.

Activity and efficiency of complexes described herein are comparable with those observed for catalysts known in the literature. It was unexpectedly found that residual Ru can be simply and efficiently removed from reaction mixture or from crude product using an inexpensive purification method when complexes bearing hydroxamic acid ester group are applied as a catalysts.

BRIEF DESCRIPTION

This disclosure relates to new metal complexes, their application in olefin or alkyne metathesis and to methods of carrying out olefin metathesis reactions.

Some embodiments, include a process for carrying out a metathesis reaction, comprising reacting a mixture comprising: 1) two compounds each having a C=C double bond, or one compound having at least two C=C double bonds; and 2) a catalyst.

Some embodiments include a process for carrying out a metathesis reaction, comprising reacting a mixture comprising: at least one olefin and a catalyst.

New useful catalysts for metathesis reactions such as these include compounds of Formula 1:

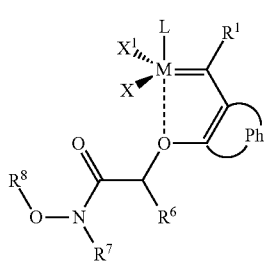

Formula 1 wherein M is ruthenium or osmium; X and $X^1$ are independently anionic ligands; L is neutral ligand; $R^1$ is hydrogen, $C_{1-20}$ alkyl, or $C_{5-10}$ aryl;

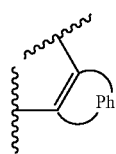

is optionally substituted o-phenylene, wherein 2 or more substituents of the o-phenylene may form an optionally substituted fused $C_{4-8}$ carbocyclic ring an optionally substituted fused aromatic $C_{5-14}$ ring; and $R^6$, $R^7$, and $R^8$ are independently H, $C_{1-6}$ alkyl, optionally substituted $C_{4-10}$ heterocyclyl, or optionally substituted $C_{5-14}$ aryl; wherein $R^7$ and $R^8$ may be linked together to form a substituted or unsubstituted $C_{4-8}$ cyclic system.

DETAILED DESCRIPTION

In addition to Formula 1, useful catalysts may be represented by any of Formulas 2-16.

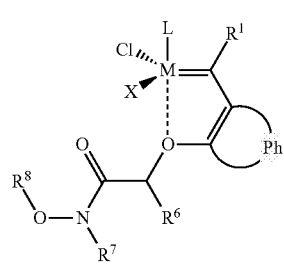

Formula 2

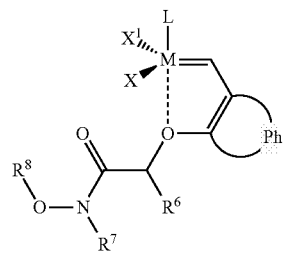

Formula 3

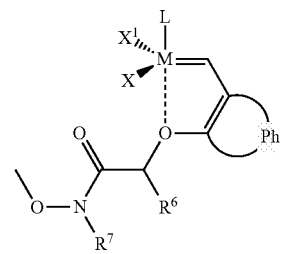

Formula 4

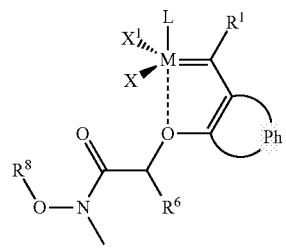

Formula 5

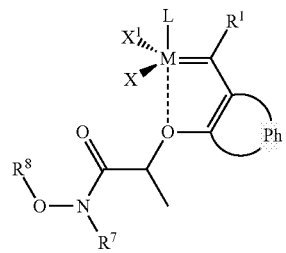

Formula 6

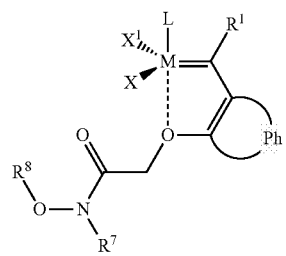

Formula 7

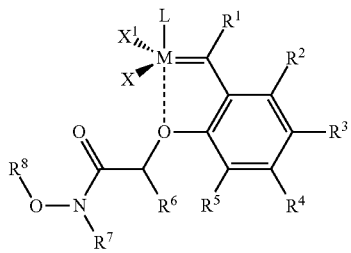

Formula 8

Formula 9
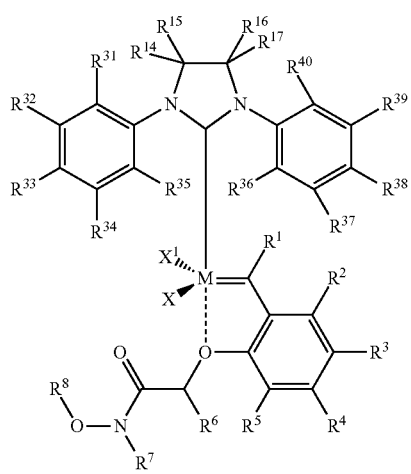
Formula 10
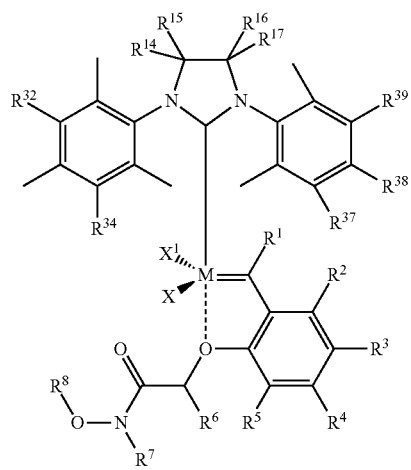
Formula 11
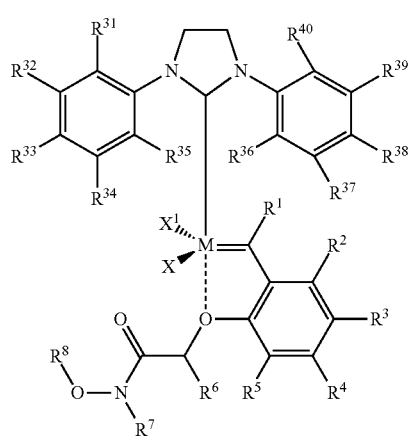
Formula 12
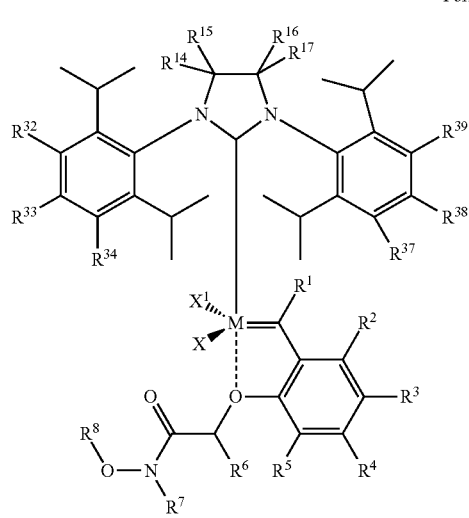
Formula 13
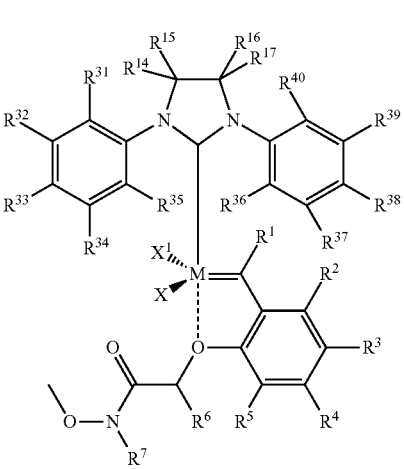
Formula 14
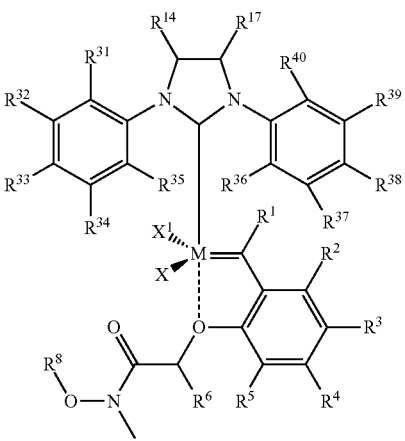

Formula 15

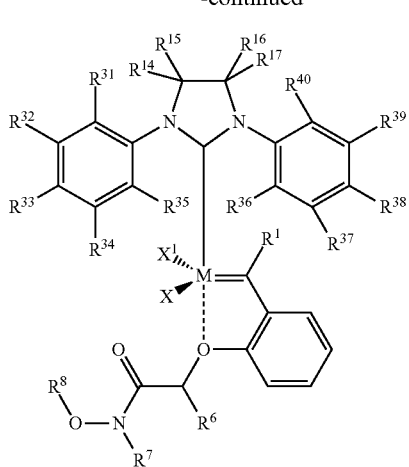

Formula 16

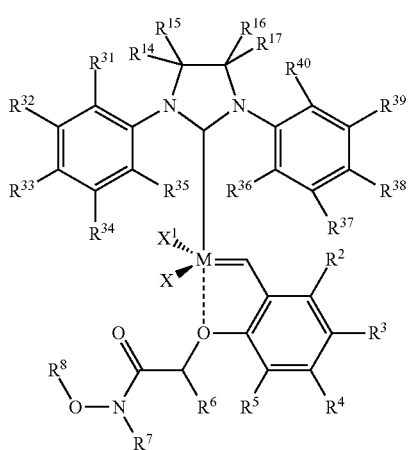

With respect to any relevant formula or structural representation herein, such as Formulas 1-6,

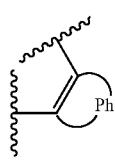

may be optionally substituted o-phenylene, wherein 2 or more substituents of the o-phenylene may form an optionally substituted fused $C_{4-8}$ carbocyclic ring or an optionally substituted fused aromatic $C_{5-14}$ ring. If substituted, any suitable substituent may be present on the o-phenylene, such as a substituent with a molecular weight of 15 g/mol to 1000 g/mol, 15 g/mol to 500 g/mol, 15 g/mol to 100 g/mol, or 15 g/mol to 50 g/mol. In some embodiments, all substituents of the o-phenylene have a molecular weight of 15 g/mol to 1000 g/mol, 15 g/mol to 500 g/mol, 15 g/mol to 100 g/mol, or 15 g/mol to 50 g/mol. In some embodiments, one, more than one, or all of the substituents may independently be H; F; Cl; Br; I; $C_{1-20}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc, $C_{2-20}$ alkenyl; $C_{2-20}$ alkynyl; $C_{5-10}$ aryl; $C_{1-20}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc; $C_{2-20}$ alkenyloxy; $C_{2-20}$ alkynyloxy; $C_{5-10}$ aryloxy; $C_{1-20}$ alkoxycarbonyl; $C_{1-20}$ alkylamino; $C_{1-20}$ protonated alkylamino; amino; protonated amino; $C_{1-20}$ alkylammonium; nitro; carboxy; amido; sulfonamido; or $C_{1-20}$ perhaloalkyl; those groups can be optionally substituted with $C_{1-20}$ alkyl, $C_{1-20}$ perhaloalkyl, $C_{5-10}$ aryl, or $C_{4-10}$ quaternized heterocyclic. Two or more substituents of the o-phenylene may be linked together to form a substituted or unsubstituted fused $C_{4-8}$ carbocyclic ring, or a substituted or unsubstituted fused aromatic $C_{5-14}$ ring. In some embodiments, the o-phenylene is unsubstituted, or all substituents are $CH_3$, $C_2H_5$, $C_3H_7$, $C_4H_9$, —$OCH_3$, —$OC_2H_5$, —$OC_3H_7$, —$OC_4H_9$, F, Cl, $NO_2$, or CN. In some embodiments, the o-phenylene is unsubstituted. In some embodiments, the o-phenylene has a single $NO_2$ substituent and no other substituents.

With respect to any relevant formula or structural representation herein, such as Formulas 1-16, M may be ruthenium or osmium. In some embodiments, M is ruthenium. In some embodiments, M is osmium.

With respect to any relevant formula or structural representation herein, such as Formulas 1-16, X may be an anionic ligand, such as $F^-$, $Cl^-$, $Br^-$, $I^-$, $^-OR^9$, $^-O(C=O)R^9$, or $^-O(SO_2)R^9$. In some embodiments, X is $Cl^-$.

With respect to any relevant formula or structural representation herein, such as Formulas 1-16, $X^1$ may be an anionic ligand, such as $F^-$, $Cl^-$, $Br^-$, $I^-$, $^-OR^9$, $^-O(C=O)R^9$, or $^-O(SO_2)R^9$. In some embodiments, $X^1$ is $Cl^-$.

With respect to any relevant formula or structural representation herein, such as Formulas 1-16, L may be a neutral ligand, such as a carbene, an amine, or a phosphine. In some embodiments, L is an optionally substituted trialkylphosphine or an optionally substituted 1,3-diphenyldihydroimidazol-2-ylidene. In some embodiments, L is $P(R^{18})(R^{19})(R^{20})$.

With respect to any relevant formula or structural representation herein, such as Formulas 1-16, in some embodiments L is N-heterocyclic carbene ligand (NHC), such as an NHC shown below.

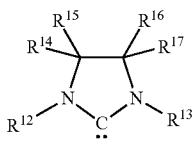

2a

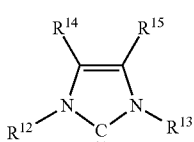

2b

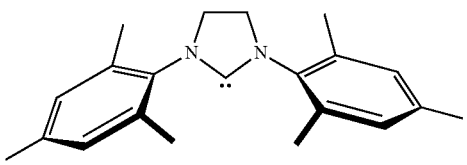

2c

-continued

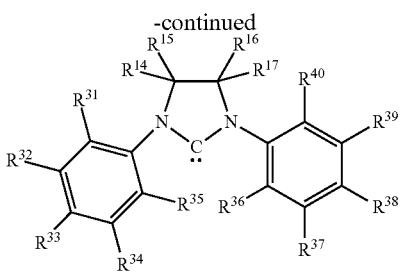

2d

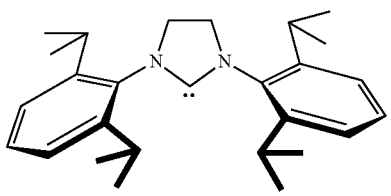

With respect to any relevant formula or structural representation herein, such as Formulas 1-8, in some embodiments L is tricyclohexylphosphine.

In some embodiments, L is

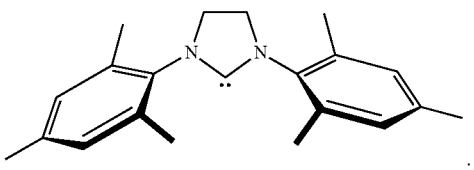

In some embodiments, L is

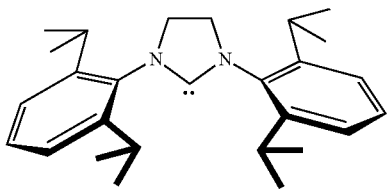

With respect to any relevant formula or structural representation herein, such as Formulas 1, 2 and 5-15, $R^1$ may be hydrogen; $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; or $C_{5-10}$ aryl, such as optionally substituted phenyl.

With respect to any relevant formula or structural depiction herein, such as Formulas 8-16, $R^2$ may be H or any substituent, including any substituent having a molecular weight of 15 g/mol to 3000 g/mol, such as H; F; Cl; Br; I; $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{2-20}$ alkenyl; $C_{2-20}$ alkynyl; $C_{5-10}$ aryl, such as phenyl or naphthyl; $C_{1-20}$ alkoxy, such as $-OCH_3$, $-OC_2H_5$, $-OC_3H_7$, cyclic $-OC_3H_5$, $-OC_4H_9$, cyclic $-OC_4H_7$, $-OC_5H_{11}$, cyclic $-OC_5H_9$, $-OC_6H_{13}$, cyclic $-OC_6H_{11}$, etc; $C_{2-20}$ alkenyloxy; $C_{2-20}$ alkynyloxy; $C_{5-10}$ aryloxy, such as phenoxy; $C_{1-20}$ alkoxycarbonyl; $C_{1-20}$ alkylamino; $C_{1-20}$ protonated alkylamino; amino; protonated amino; $C_{1-20}$ alkylammonium; nitro; carboxy; amido; sulfonamido; or $C_{1-20}$ perhaloalkyl; those groups can be optionally substituted with $C_{1-20}$ alkyl; $C_{1-20}$ perhaloalkyl; $C_{5-10}$ aryl; or $C_{4-10}$ quaternized heterocyclic. In some embodiments, $R^2$ is H, F, Cl, Br, I, $C_{1-12}$ perfluoroalkyl, or a substituent having 1 to 12 carbon atoms, 0 to 3 oxygen atoms, 0 to 3 nitrogen atoms, 0 to 3 sulfur atoms, and 0 to 41 hydrogen atoms. In some embodiments, $R^2$ is H, F, Cl, $CH_3$, $C_2H_5$, $C_3H_7$, $-OCH_3$, $-OC_2H_5$, $-OC_3H_7$, or $NO_2$. In some embodiments, $R^2$ is a moiety with a molecular weight of 1 g/mol to 100 g/mol or 1 g/mol to 50 g/mol. In some embodiments, $R^2$ is H.

With respect to any relevant formula or structural depiction herein, such as Formulas 8-16, $R^3$ may be H or any substituent, including any substituent having a molecular weight of 15 g/mol to 3000 g/mol, such as H; F; Cl; Br; I; $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{2-20}$ alkenyl; $C_{2-20}$ alkynyl; $C_{5-10}$ aryl, such as phenyl or naphthyl; $C_{1-20}$ alkoxy, such as $-OCH_3$, $-OC_2H_5$, $-OC_3H_7$, cyclic $-OC_3H_5$, $-OC_4H_9$, cyclic $-OC_4H_7$, $-OC_5H_{11}$, cyclic $-OC_5H_9$, $-OC_6H_{13}$, cyclic $-OC_6H_{11}$, etc; $C_{2-20}$ alkenyloxy; $C_{2-20}$ alkynyloxy; $C_{5-10}$ aryloxy, such as phenoxy; $C_{1-20}$ alkoxycarbonyl; $C_{1-20}$ alkylamino; $C_{1-20}$ protonated alkylamino; amino; protonated amino; $C_{1-20}$ alkylammonium; nitro; carboxy; amido; sulfonamido; or $C_{1-20}$ perhaloalkyl; those groups can be optionally substituted with $C_{1-20}$ alkyl; $C_{1-20}$ perhaloalkyl; $C_{5-10}$ aryl; or $C_{4-10}$ quaternized heterocyclic. In some embodiments, $R^3$ is H, F, Cl, Br, I, $C_{1-12}$ perfluoroalkyl, or a substituent having 1 to 12 carbon atoms, 0 to 3 oxygen atoms, 0 to 3 nitrogen atoms, 0 to 3 sulfur atoms, and 0 to 41 hydrogen atoms. In some embodiments, $R^3$ is H, F, Cl, $CH_3$, $C_2H_5$, $C_3H_7$, $-OCH_3$, $-OC_2H_5$, $-OC_3H_7$, or $NO_2$. In some embodiments, $R^3$ is a moiety with a molecular weight of 1 g/mol to 100 g/mol or 1 g/mol to 50 g/mol. In some embodiments, $R^3$ is $NO_2$. In some embodiments, $R^3$ is H.

With respect to any relevant formula or structural depiction herein, such as Formulas 8-16, $R^4$ may be H or any substituent, including any substituent having a molecular weight of 15 g/mol to 3000 g/mol, such as H; F; Cl; Br; I; $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{2-20}$ alkenyl; $C_{2-20}$ alkynyl; $C_{5-10}$ aryl, such as phenyl or naphthyl; $C_{1-20}$ alkoxy, such as $-OCH_3$, $-OC_2H_5$, $-OC_3H_7$, cyclic $-OC_3H_5$, $-OC_4H_9$, cyclic $-OC_4H_7$, $-OC_5H_{11}$, cyclic $-OC_5H_9$, $-OC_6H_{13}$, cyclic $-OC_6H_{11}$, etc; $C_{2-20}$ alkenyloxy; $C_{2-20}$ alkynyloxy; $C_{5-10}$ aryloxy, such as phenoxy; $C_{1-20}$ alkoxycarbonyl; $C_{1-20}$ alkylamino; $C_{1-20}$ protonated alkylamino; amino; protonated amino; $C_{1-20}$ alkylammonium; nitro; carboxy; amido; sulfonamido; or $C_{1-20}$ perhaloalkyl; those groups can be optionally substituted with $C_{1-20}$ alkyl; $C_{1-20}$ perhaloalkyl; $C_{5-10}$ aryl; or $C_{4-10}$ quaternized heterocyclic. In some embodiments, $R^4$ is H, F, Cl, Br, I, $C_{1-12}$ perfluoroalkyl, or a substituent having 1 to 12 carbon atoms, 0 to 3 oxygen atoms, 0 to 3 nitrogen atoms, 0 to 3 sulfur atoms, and 0 to 41 hydrogen atoms. In some embodiments, $R^4$ is H, F, Cl, $CH_3$, $C_2H_5$, $C_3H_7$, $-OCH_3$, $-OC_2H_5$, $-OC_3H_7$, or $NO_2$. In some embodiments, $R^4$ is a moiety with a molecular weight of 1 g/mol to 100 g/mol or 1 g/mol to 50 g/mol. In some embodiments, $R^4$ is H.

With respect to any relevant formula or structural depiction herein, such as Formulas 8-16, $R^5$ may be H or any substituent, including any substituent having a molecular weight of 15 g/mol to 3000 g/mol, such as H; F; Cl; Br; I; $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{2-20}$ alkenyl; $C_{2-20}$ alkynyl; $C_{5-10}$ aryl, such as phenyl or naphthyl; $C_{1-20}$ alkoxy, such as $-OCH_3$, $-OC_2H_5$, —OC$_3$H$_7$, cyclic —OC$_3$H$_5$, —OC$_4$H$_9$, cyclic —OC$_4$H$_7$, —OC$_5$H$_{11}$, cyclic —OC$_5$H$_9$, —OC$_6$H$_{13}$, cyclic —OC$_6$H$_{11}$, etc; C$_{2-20}$ alkenyloxy; C$_{2-20}$ alkynyloxy; C$_{5-10}$ aryloxy, such as phenoxy; C$_{1-20}$ alkoxycarbonyl; C$_{1-20}$ alkylamino; C$_{1-20}$ protonated alkylamino; amino; protonated amino; C$_{1-20}$ alkylammonium; nitro; carboxy; amido; sulfonamido; or C$_{1-20}$ perhaloalkyl; those groups can be optionally substituted with C$_{1-20}$ alkyl; C$_{1-20}$ perhaloalkyl; C$_{5-10}$ aryl; or C$_{4-10}$ quaternized heterocyclic. In some embodiments, R$^5$ is H, F, Cl, Br, I, C$_{1-12}$ perfluoroalkyl, or a substituent having 1 to 12 carbon atoms, 0 to 3 oxygen atoms, 0 to 3 nitrogen atoms, 0 to 3 sulfur atoms, and 0 to 41 hydrogen atoms. In some embodiments, R$^5$ is H, F, Cl, CH$_3$, C$_2$H$_5$, C$_3$H$_7$, —OCH$_3$, —OC$_2$H$_5$, —OC$_3$H$_7$, or NO$_2$. In some embodiments, R$^5$ is a moiety with a molecular weight of 1 g/mol to 100 g/mol or 1 g/mol to 50 g/mol. In some embodiments, R$^5$ is H.

In some embodiments, 2 or more of R$^2$, R$^3$, R$^4$, and R$^5$ may be linked together to form a substituted or unsubstituted fused C$_{4-8}$ carbocyclic ring, or a substituted or unsubstituted fused aromatic C$_{5-14}$ ring.

With respect to any relevant formula or structural representation herein, R$^6$ may be hydrogen; C$_{1-6}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.; optionally substituted C$_{4-10}$ heterocyclyl, or optionally substituted C$_{5-14}$ aryl. In some embodiments, R$^6$ is C$_{1-6}$ alkyl. In some embodiments, R$^6$ is H, methyl, ethyl, propyl, or isopropyl. In some embodiments, R$^6$ is H. In some embodiments, R$^6$ is methyl.

With respect to any relevant formula or structural representation herein, R$^7$ may be hydrogen; C$_{1-6}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.; optionally substituted C$_{4-10}$ heterocyclyl, or optionally substituted C$_{5-14}$ aryl; wherein R$^7$ and R$^8$ may be linked together to form a substituted or unsubstituted C$_{4-8}$ cyclic system. In some embodiments, R$^7$ is H, methyl, ethyl, propyl, or isopropyl. In some embodiments, R$^7$ is H. In some embodiments, R$^7$ is methyl.

With respect to any relevant formula or structural representation herein, R$^8$ may be hydrogen; C$_{1-6}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.; optionally substituted C$_{4-10}$ heterocyclyl, or optionally substituted C$_{5-14}$ aryl; wherein R$^7$ and R$^8$ may be linked together to form a substituted or unsubstituted C$_{4-8}$ cyclic system. In some embodiments, R$^8$ is C$_{1-6}$ alkyl. In some embodiments, R$^8$ is H, methyl, ethyl, propyl, or isopropyl. In some embodiments, R$^8$ is H. In some embodiments, R$^8$ is methyl.

With respect to any relevant formula or structural representation herein, each R$^9$ may independently be C$_1$-C$_{12}$ alkyl (such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.) or C$_5$-C$_{14}$ aryl, wherein R$^9$ may be optionally substituted with C$_1$-C$_6$ alkyl, C$_1$-C$_6$ perhaloalkyl, C$_1$-C$_6$ alkoxy, F, Cl, Br, or I.

With respect to any relevant formula or structural representation herein, such as Formula 2a or Formula 2b, R$^{12}$ may be optionally substituted C$_5$-C$_{14}$ aryl, such as phenyl. Any substituent may be present on the aryl. In some embodiments, the aryl is optionally substituted with at least one C$_1$-C$_{12}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.; C$_1$-C$_{12}$ perhaloalkyl, such as CF$_3$, C$_2$F$_5$, C$_3$F$_7$, cyclic C$_3$F$_5$, C$_4$F$_9$, cyclic C$_4$F$_7$, C$_5$F$_{11}$, cyclic C$_5$F$_9$, C$_6$F$_{13}$, cyclic C$_6$F$_{11}$, etc.; C$_1$-C$_{12}$ alkoxy, such as such as —OCH$_3$, —OC$_2$H$_5$, —OC$_3$H$_7$, cyclic —OC$_3$H$_5$, —OC$_4$H$_9$, cyclic —OC$_4$H$_7$, —OC$_5$H$_{11}$, cyclic —OC$_5$H$_9$, —OC$_6$H$_{13}$, cyclic —OC$_6$H$_{11}$, etc.; or halide, such as F, Cl, Br, I. In some embodiments, R$^{12}$ is optionally substituted phenyl. In some embodiments, R$^{12}$ is phenyl optionally substituted with methyl, ethyl, propyl, isopropyl, butyl, or an isomer of butyl. In some embodiments, R$^{12}$ is 2,6-diisopropylphenyl. In some embodiments, R$^{12}$ is 2,4,6-trimethylphenyl.

With respect to any relevant formula or structural representation herein, such as Formula 2a or Formula 2b, R$^{13}$ may be optionally substituted C$_5$-C$_{14}$ aryl, such as phenyl. Any substituent may be present on the aryl. In some embodiments, the aryl is optionally substituted with at least one C$_1$-C$_{12}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.; C$_1$-C$_{12}$ perhaloalkyl, such as CF$_3$, C$_2$F$_5$, C$_3$F$_7$, cyclic C$_3$F$_5$, C$_4$F$_9$, cyclic C$_4$F$_7$, C$_5$F$_{11}$, cyclic C$_5$F$_9$, C$_6$F$_{13}$, cyclic C$_6$F$_{11}$, etc.; C$_1$-C$_{12}$ alkoxy, such as such as —OCH$_3$, —OC$_2$H$_5$, —OC$_3$H$_7$, cyclic —OC$_3$H$_5$, —OC$_4$H$_9$, cyclic —OC$_4$H$_7$, —OC$_5$H$_{11}$, cyclic —OC$_5$H$_9$, —OC$_6$H$_{13}$, cyclic —OC$_6$H$_{11}$, etc.; or halide, such as F, Cl, Br, I. In some embodiments, R$^{13}$ is optionally substituted phenyl. In some embodiments, R$^{13}$ is phenyl optionally substituted with methyl, ethyl, propyl, isopropyl, butyl, or an isomer of butyl. In some embodiments, R$^{13}$ is 2,6-diisopropylphenyl. In some embodiments, R$^{13}$ is 2,4,6-trimethylphenyl.

With respect to any relevant formula or structural representation herein, such as Formulas 2a, 2b, and 9-16, R$^{14}$ may be hydrogen or C$_1$-C$_{12}$ alkyl, such as CH$_3$, C$_2$H$_5$, C$_3$H$_7$, cyclic C$_3$H$_5$, etc. In some embodiments, R$^{14}$ is H.

With respect to any relevant formula or structural representation herein, such as Formulas 2a, 2b, and 9-16, R$^{15}$ may be hydrogen or C$_1$-C$_{12}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc. In some embodiments, R$^{15}$ is H.

With respect to any relevant formula or structural representation herein, such as Formulas 2a, 2b, and 9-16, R$^{16}$ may be hydrogen or C$_1$-C$_{12}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, etc. In some embodiments, R$^{16}$ is H.

With respect to any relevant formula or structural representation herein, such as Formulas 2a, 2b, and 9-16, R$^{17}$ may be hydrogen or C$_1$-C$_{12}$ alkyl, such as CH$_3$, C$_2$H$_5$, C$_3$H$_7$, cyclic C$_3$H$_5$, etc. In some embodiments, R$^{17}$ is H.

With respect to any relevant formula or structural representation herein, R$^{18}$, R$^{19}$, and R$^{20}$ are independently C$_{1-12}$ alkyl (such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.), C$_{1-12}$ alkoxy (such as —OCH$_3$, —OC$_2$H$_5$, —OC$_3$H$_7$, cyclic —OC$_3$H$_5$, —OC$_4$H$_9$, cyclic —OC$_4$H$_7$, —OC$_5$H$_{11}$, cyclic —OC$_5$H$_9$, —OC$_6$H$_{13}$, cyclic —OC$_6$H$_{11}$, etc.), C$_{5-12}$ aryl (such as optionally substituted phenyl), C$_{5-12}$ aryloxy, or C$_{5-12}$ heterocyclic; wherein 2 of R$^{18}$, R$^{19}$ and R$^{20}$ may optionally be linked together to form cyclic system.

With respect to any relevant formula or structural representation herein, such as Formulas 9, 11, and 13-16, R$^{31}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. Some examples of (C$_{3-10}$N$_{1-2}$O$_{0-1}$H$_{9-23}$)$^+$A$^-$ include (C$_3$NH$_9$)$^+$Cl$^-$ (or [N(CH$_3$)$_4$$^+$]Cl$^-$), (C$_4$NH$_{12}$)$^+$Cl$^-$ (such as [—CH$_2$N(CH$_3$)$_3$]$^+$ Cl$^-$ or [—N(CH$_3$)$_2$CH$_2$CH$_3$]$^+$Cl$^-$), etc. In some embodiments R$^{31}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{31}$ is H. In some embodiments R$^{31}$ is methyl. In some embodiments, R$^{31}$ is isopropyl.

With respect to any relevant formula or structural representation herein, such as Formulas 9-16, R$^{32}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{0-23}$)$^+$A$^-$, wherein A$^-$ is an appropriate anion. In some embodiments R$^{32}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{32}$ is H.

With respect to any relevant formula or structural representation herein, such as Formulas 9 and 11-16, R$^{33}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{33}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{33}$ is H. In some embodiments, R$^{33}$ is methyl.

With respect to any relevant formula or structural representation herein, such as Formulas 9-16, R$^{34}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{34}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{34}$ is H.

With respect to any relevant formula or structural representation herein, such as Formulas 9, 11, and 13-16, R$^{35}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{35}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{35}$ is H. In some embodiments R$^{35}$ is methyl. In some embodiments, R$^{35}$ is isopropyl.

With respect to any relevant formula or structural representation herein, such as Formulas 9, 11, and 13-16, R$^{36}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{36}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{36}$ is H. In some embodiments R$^{36}$ is methyl. In some embodiments, R$^{36}$ is isopropyl.

With respect to any relevant formula or structural representation herein, such as Formulas 9-16, R$^{37}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{34}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{37}$ is H.

With respect to any relevant formula or structural representation herein, such as Formulas 9-16, R$^{38}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{38}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{38}$ is H. In some embodiments, R$^{38}$ is methyl.

With respect to any relevant formula or structural representation herein, such as Formulas 9-16, R$^{39}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{39}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{39}$ is H.

With respect to any relevant formula or structural representation herein, such as Formulas 9, 11, and 13-16, R$^{40}$ may be H, OH, NH$_2$, F, Cl, Br, I, NO$_2$, CN, CF$_3$, C$_{1-10}$ alkyl, C$_{1-10}$ alkoxy, or a moiety having a formula (C$_{3-10}$N$_{1-2}$O$_{0-1}$H$_{9-23}$)$^+$A$^-$, wherein A$^-$ is an appropriate anion. In some embodiments R$^{40}$ is H, or has a molecular weight of 15 g/mol to 500 g/mol, 15 g/mol to 200 g/mol, 15 g/mol to 100 g/mol, or 15 g/mol to 50 g/mol. In some embodiments R$^{40}$ is H. In some embodiments R$^{40}$ is methyl. In some embodiments, R$^{40}$ is isopropyl.

Some embodiments include complexes of formula 8:
wherein M is ruthenium or osmium;
X and X$^1$ are independently any anionic ligand;
L is neutral ligand;
R$^1$ is hydrogen, C$_{1-20}$ alkyl, or C$_{5-10}$ aryl;
R$^2$, R$^3$, R$^4$, and R$^5$ are independently hydrogen, halide, C$_{1-20}$ alkyl, C$_{2-20}$ alkenyl, C$_{2-20}$ alkynyl, C$_{5-10}$ aryl, C$_{1-20}$ alkoxy, C$_{2-20}$ alkenyloxy, C$_{2-20}$ alkynyloxy, C$_{5-10}$ aryloxy, C$_{1-20}$ alkoxycarbonyl, C$_{1-20}$ alkylamino, C$_{1-20}$ protonated alkylamino, amino, protonated amino, C$_{1-20}$ alkylammonium, nitro, carboxy, amido, sulfonamido, or C$_{1-20}$ perhaloalkyl; those groups can be optionally substituted with C$_{1-20}$ alkyl, C$_{1-20}$ perhaloalkyl, or C$_{5-10}$ aryl;
Wherein 2 or more of R$^2$, R$^3$, R$^4$, and R$^5$ may be linked together to form a substituted or unsubstituted, fused 2 or more C$_{4-8}$ carbocyclic ring, or a substituted or unsubstituted fused aromatic C$_{5-14}$ ring;
R$^6$, R$^7$, and R$^8$ are independently hydrogen, C$_{1-6}$ alkyl, C$_{4-10}$ cycloalkyl, C$_{4-10}$ heterocyclyl, or C$_{5-14}$ aryl; wherein R$^7$ and R$^8$ may be linked together to form a substituted or unsubstituted C$_{4-8}$ cyclic system.

In some embodiments
M is ruthenium;
X and X$^1$ are independently halide, —OR$^9$, —O(C=O)R$^9$, or —O(SO$_2$)R$^9$, wherein R$^9$ is C$_1$-C$_{12}$ alkyl, C$_3$-C$_{12}$ cycloalkyl, or C$_5$-C$_{14}$ aryl, wherein R$^9$ may be optionally substituted with C$_1$-C$_6$ alkyl, C$_1$-C$_6$ perhaloalkyl, C$_1$-C$_6$ alkoxy, or halide;
L is N-heterocyclic carbene ligand (NHC);
R$^1$ is hydrogen or C$_{1-20}$ alkyl;
R$^2$, R$^3$, R$^4$, and R$^5$ are independently hydrogen, halide, C$_{1-20}$ alkyl, C$_{2-20}$ alkenyl, C$_{2-20}$ alkynyl, C$_{5-10}$ aryl, C$_{1-20}$ alkoxy, C$_{2-20}$ alkenyloxy, C$_{2-20}$ alkynyloxy, C$_{5-10}$ aryloxy, C$_{1-20}$ alkoxycarbonyl, C$_{1-20}$ alkylamino, C$_{1-20}$ protonated alkylamino, amino, protonated amino, C$_{1-20}$ alkylammonium, nitro, carboxy, amido, sulfonamido, or C$_{1-20}$ perhaloalkyl; those groups can be optionally substituted with C$_{1-20}$ alkyl, C$_{1-20}$ perhaloalkyl; C$_{5-10}$ aryl, or C$_{4-10}$ quaternized heterocyclic;
Wherein 2 or more of R$^2$, R$^3$, R$^4$, and R$^5$ may be linked together to form a substituted or unsubstituted fused C$_{4-8}$ carbocyclic ring, or a substituted or unsubstituted fused aromatic C$_{5-14}$ ring.
R$^6$, R$^7$, R$^8$ are independently hydrogen, C$_{1-6}$ alkyl, C$_{4-10}$ cycloalkyl, C$_{4-10}$ heterocyclic, or C$_{5-14}$ aryl; R$^7$, and R$^8$ and may be linked together to form a substituted or unsubstituted cyclic C$_{4-8}$ system.

In some embodiments
M is ruthenium;
X and X$^1$ are independently halide, —OR$^9$, —O(C=O)R$^9$, or —O(SO$_2$)R$^9$, wherein R$^9$ is C$_1$-C$_{12}$ alkyl, C$_3$-C$_{12}$ cycloalkyl, or C$_5$-C$_{14}$ aryl, moreover R$^9$ may be optionally substituted with at least one C$_1$-C$_6$ alkyl, C$_1$-C$_6$ perhaloalkyl, C$_1$-C$_6$ alkoxy or halide;
L is P(R$^{18}$)(R$^{19}$)(R$^{20}$);

wherein $R^{18}$, $R^{19}$, and $R^{20}$ are independently $C_{1-12}$ alkyl, $C_{1-12}$ alkoxy, $C_{3-12}$ cycloalkyl, $C_{5-12}$ aryl, $C_{5-12}$ aryloxy, or $C_{5-12}$ heterocyclic; wherein 2 of $R^{18}$, $R^{19}$ and $R^{20}$ may optionally be linked together to form cyclic system;

$R^1$ is hydrogen or $C_{1-20}$ alkyl;

$R^2$, $R^3$, $R^4$, and $R^5$ are independently hydrogen, halide, $C_{1-20}$ alkyl, $C_{2-20}$ alkenyl, $C_{2-20}$ alkynyl, $C_{5-10}$ aryl, $C_{1-20}$ alkoxy, $C_{2-20}$ alkenyloxy, $C_{2-20}$ alkynyloxy, $C_{5-10}$ aryloxy, $C_{1-20}$ alkoxycarbonyl, $C_{1-20}$ alkylamino, $C_{1-20}$ protonated alkylamino, amino, protonated amino, $C_{1-20}$ alkylammonium, nitro, carboxy, amido, sulfonamido, or $C_{1-20}$ perhaloalkyl; those groups can be optionally substituted with $C_{1-20}$ alkyl, $C_{1-20}$ perhaloalkyl, $C_{5-10}$ aryl, or $C_{4-10}$ quaternized heterocyclic;

Wherein 2 or more of $R^2$, $R^3$, $R^4$, and $R^5$ may be linked together to form a substituted or unsubstituted fused $C_{4-8}$ carbocyclic ring, or a substituted or unsubstituted fused aromatic $C_{5-14}$ ring;

$R^6$, $R^7$, and $R^8$ are independently hydrogen, $C_{1-6}$ alkyl, $C_{4-10}$ cycloalkyl, $C_{4-10}$ heterocyclic, or $C_{5-14}$ aryl; wherein $R^7$ and $R^8$ may be linked together to form a substituted or unsubstituted $C_{4-8}$ cyclic system.

In some embodiments

M is ruthenium;

X and $X^1$ are independently halide;

L is N-heterocyclic carbene ligand (NHC) of formulae 2a or 2b:

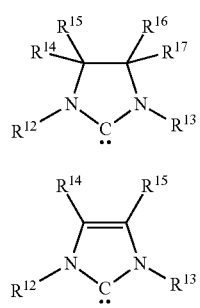

wherein:

$R^{12}$ and $R^{13}$ are independently $C_5$-$C_{14}$ aryl, optionally substituted with at least one $C_1$-$C_{12}$ alkyl, $C_1$-$C_{12}$ perhaloalkyl, $C_1$-$C_{12}$ alkoxy or halide;

$R^{14}$, $R^{15}$, $R^{16}$, and $R^{17}$ are independently hydrogen or $C_1$-$C_{12}$ alkyl;

$R^1$ is hydrogen;

$R^2$, $R^3$, $R^4$, and $R^5$ are independently hydrogen, halide, nitro, carboxy, amido, sulfonamido, or $C_{1-20}$ perhaloalkyl; those groups may be optionally substituted with at least one $C_{1-20}$ alkyl, $C_{1-20}$ perhaloalkyl, or $C_{5-10}$ aryl; wherein 2 or more of $R^2$, $R^3$, $R^4$, and $R^5$ may be linked together to form a substituted or unsubstituted fused $C_{4-8}$ carbocyclic ring, or a substituted or unsubstituted fused aromatic $C_{5-14}$ ring;

$R^6$, $R^7$, and $R^8$ are independently hydrogen, $C_{1-6}$ alkyl, $C_{4-10}$ cycloalkyl, $C_{4-10}$ heterocyclic, or $C_{5-14}$ aryl; wherein $R^7$ and $R^8$ may be linked together to form a substituted or unsubstituted $C_{4-8}$ cyclic system.

In some embodiments

M is ruthenium;

X and $X^1$ are chloride;

L is an N-heterocyclic carbene ligand (NHC) of formulae 2c or 2d:

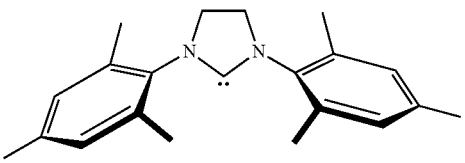

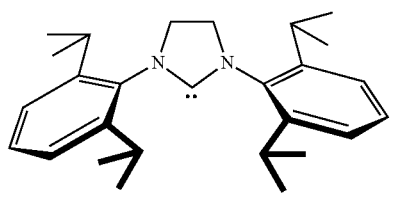

$R^1$ is hydrogen;

$R^2$, $R^3$, $R^4$, and $R^5$ are independently hydrogen or nitro;

$R^6$, $R^7$, and $R^8$ are independently hydrogen, $C_{1-6}$ alkyl, or $C_{5-14}$ aryl;

$R^7$ and $R^8$ may be linked together to form a substituted or unsubstituted $C_{4-8}$ cyclic system.

In some embodiments $R^6$, $R^7$, and $R^8$ are independently hydrogen or methyl.

Some embodiments include one of the following compounds: 1.

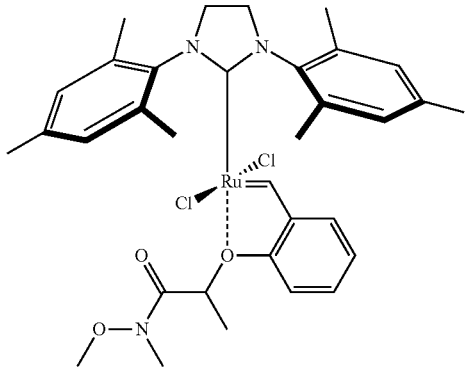

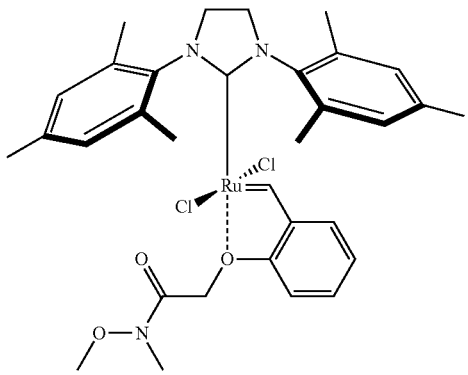

-continued

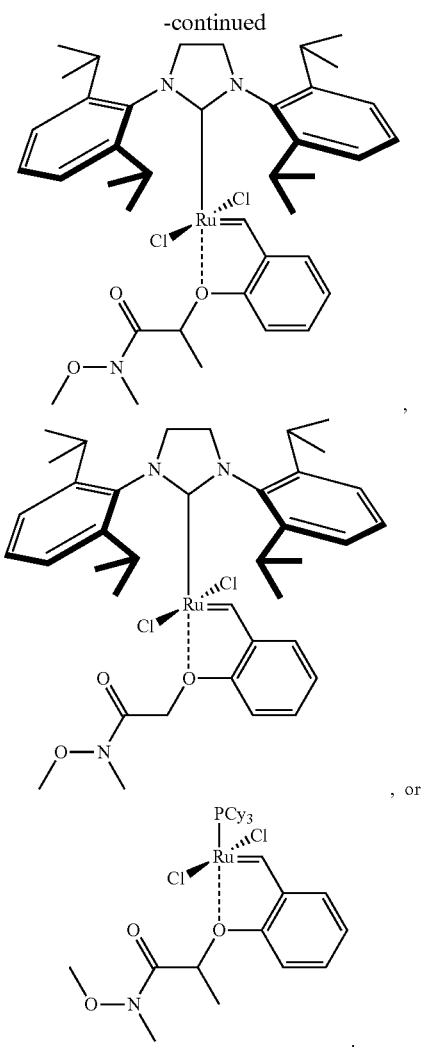

, or

Further embodiments relate to the application of complexes of any of Formulas 1-16, wherein all substituents are described above, as a catalysts for olefin metathesis. Examples of olefin metathesis reactions in which complexes described herein can be used are ring closing metathesis (RCM), cross metathesis (CM), homometathesis and alken-alkyn (en-yn) metathesis.

In some embodiments, complexes of any of Formulas 1-16 are used as a catalyst in ring opening metathesis polymerization (ROMP).

Further embodiments relate to the method of carrying out of metathesis reaction, wherein at least one olefin is contacted with a complex of any of Formulas 1-16, wherein all substituents are described above.

In some embodiments, metathesis reaction is carried out in an organic solvent.

In some embodiments, metal impurities are removed from product by filtration of reaction mixture through a pad of appropriate adsorbent.

In some embodiments, metal impurities are removed from reaction mixture by addition of adsorbent to the reaction mixture and filtration.

In some embodiments, the adsorbent is silica gel, aluminium oxide, activated aluminium oxide, diatomite, or activated carbon.

In some embodiments the adsorbent is silica gel.

In some embodiments metal impurities are removed from product by crystallization from polar solvent. Examples of suitable polar solvents include but are not limited to: methanol, ethanol, 2-propanol, ethyl acetate, water, etc.

All terms have the broadest ordinary meaning known in the art.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by ⊸ attachment may occur at any position normally occupied by a hydrogen atom.

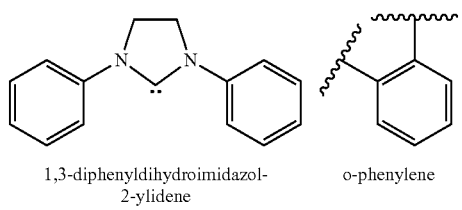

1,3-diphenyldihydroimidazol-2-ylidene        o-phenylene

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—CH$_3$), ethyl (—CH$_2$CH$_3$), n-propyl (—CH$_2$CH$_2$CH$_3$), n-butyl (—CH$_2$CH$_2$CH$_2$CH$_3$), n-pentyl (—CH$_2$CH$_2$CH$_2$CH$_2$CH$_3$), n-hexyl (—CH$_2$CH$_2$CH$_2$CH$_2$CH$_2$CH$_3$), etc.; C$_{3\text{-}10}$ branched alkyl, such as C$_3$H$_7$ (e.g. iso-propyl), C$_4$H$_9$ (e.g. branched butyl isomers), C$_5$H$_{11}$ (e.g. branched pentyl isomers), C$_6$H$_{13}$ (e.g. branched hexyl isomers), C$_7$H$_{15}$ (e.g. heptyl isomers), etc.; C$_{3\text{-}10}$ cycloalkyl, such as C$_3$H$_5$ (e.g. cyclopropyl), C$_4$H$_7$ (e.g. cyclobutyl isomers such as cyclobutyl, methylcyclopropyl, etc.), C$_5$H$_9$ (e.g. cyclopentyl isomers such as cyclopentyl, methylcyclobutyl, dimethylcyclopropyl, etc.) C$_6$H$_{11}$ (e.g. cyclohexyl isomers), C$_7$H$_{13}$ (e.g. cycloheptyl isomers), etc.; and the like.

In the groups, radicals, or moieties defined herein, the number of carbon atoms is often specified preceding the group, for example, C$_{1\text{-}6}$ alkyl means an alkyl group or radical having from 1 to 6 carbon atoms. Unless otherwise specified below, conventional definitions of terms control and conventional stable atom valences are presumed and achieved in all formulas and groups.

With respect to an optionally substituted moiety such as optionally substituted alkyl, a phrase such as "optionally substituted C$_{1\text{-}12}$ alkyl" refers to a C$_{1\text{-}12}$ alkyl that may be unsubstituted, or may have 1 or more substituents, and does not limit the number of carbon atoms in any substituent.

Substituents on alkyl may be the same as those described generally above, except that alkyl may not have an alkyl substituent. In some embodiments, substituents on alkyl are independently selected from F, Cl, Br, I, CN, CO$_2$H, —O-alkyl, ester groups, acyl, amine groups, and amide groups, and may have a molecular weight of about 15 to about 100 or about 500.

As used herein the term "aryl" has the broadest meaning generally understood in the art, and may include an aromatic ring or aromatic ring system such as phenyl, naphthyl, etc.

Unless otherwise indicated, any reference to a compound herein by structure, name, or any other means, includes salts, such as sodium, potassium, and ammonium salts; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction includes any stereoisomer or any mixture of stereoisomers.

The term "halogen" as used herein means a halogen such as fluoro, chloro, bromo, iodo, etc.

The term "alkylamino" as used herein, means the same as describe for term "alkyl" except that one or more hydrogen atoms is substituted with amine. The term "alkylamino" include but are not limited to:
—CH$_2$NMe$_2$, —CH$_2$NEt$_2$, —CH$_2$CH$_2$NMe$_2$, —CH$_2$CH$_2$NEt$_2$, —NMe$_2$, —NEt$_2$, etc.

The term "alkylammonium" as used herein, means the same as describe for term "alkyl" except that one or more hydrogen atom is substituted with ammonium group. The term "alkylammonium" include but are not limited to:

—CH$_2$NMe$_3^{\oplus}$X$^{2\ominus}$, —CH$_2$NEt$_2$Me$^{\oplus}$X$^{2\ominus}$, —CH$_2$CH$_2$NMe$_3^{\oplus}$X$^{2\ominus}$, —CH$_2$CH$_2$NEt$_2$Me$^{\oplus}$X$^{2\ominus}$, —NMe$_3^{\oplus}$X$^2$, —NEt$_2$Me$^{\oplus}$X$^2$, etc.

The term "alkenyl" as used herein, either alone or in combination with another substituent, means cyclic or acyclic, straight or branched chain alkenyl substituents. The term "alkenyl" include but are not limited to: vinyl, allenyl, etc.

The term "alkynyl" as used herein, either alone or in combination with another substituent, means cyclic or acyclic, straight or branched chain alkynyl substituents. The term "alkynyl" include but are not limited to: ethynyl, propynyl, butynyl, etc.

The term "neutral ligands" as used herein means ligands that are neutral, with respect to charge, when formally removed from the metal in their closed shell electronic state. Formal neutral ligands contain at least one lone pair of electrons, π-bond or σ bond that are capable of binding to the transition metal. Formal neutral ligands may also be polydentate when more than one formal neutral ligand is connected via a bond or a hydrocarbyl, substituted hydrocarbyl or a functional group tether. A formal neutral ligand may be a substituent of another metal compound, either the same or different, such that multiple compounds are bound together.

The term "anionic ligand" relates to the substituent capable of coordinating to the metallic center and bearing the charge which compensates the charge of metallic center, with the provision that the compensation can be full or partial. Anionic ligands include but are not limited to: fluoride, chloride, bromide, iodide, anions of carboxylic acids, anions of alcohols and phenols, etc. Anionic ligands (X, X$^1$) can be bonded together to form bidentate ligand (X—X$^1$) and additionally they can be bonded with neutral ligand to form tridentate ligand (X—X$^1$-L). An example of bidentate ligand is an anion of 2-hydroxybenzoic acid.

The term "carbene" relates to the substituent having neutral carbon atom with the number of valence equal two and two unpaired valence electrons. The term "carbene" relates also to the analogues of carbene, in which carbon atom is replaced by another chemical element, such as: boron, silicon, nitrogen, phosphorus, sulfur. One example of a carbine includes the N-heterocyclic carbene ligand (NHC). Additional examples of carbenes include but are not limited to:

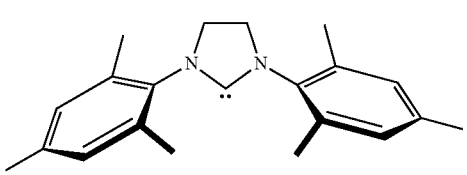

2c

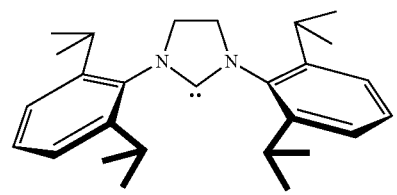

2d

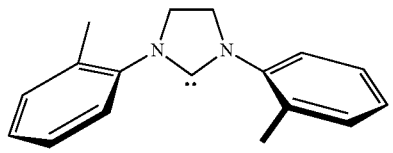

2e

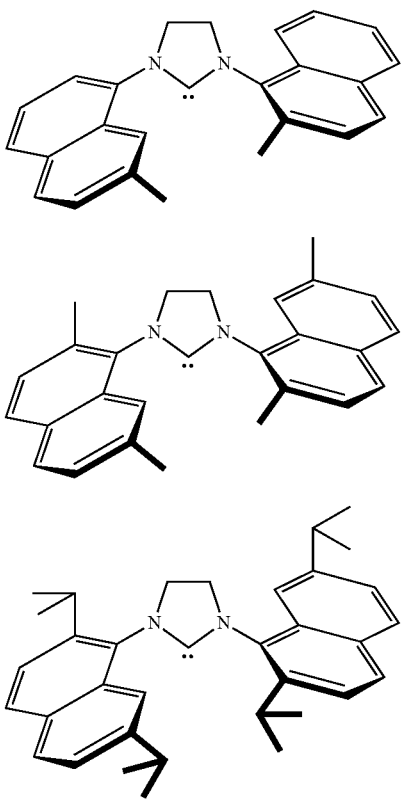

Complexes described herein can be synthesized with good results using procedures known in the literature.

These complexes are active and efficient catalysts of olefin metathesis, and their high affinity to the adsorbents (especially to the silica gel) may allow for easy removal of residual ruthenium from reaction mixture or crude product. During metathesis reactions, these metal complexes are contacted with substrates at conditions appropriate for this kind of reaction. Usually reactions are run at conditions applied also for complexes known in the literature. Average catalyst loading ranging between about 0.2 and about 5 mol %, the temperature used may be between about 0° C. to about 120° C. and the reaction time may be from about 0.1 to about 96 h.

Complexes described herein can be used in ring closing metathesis (RCM), cross metathesis (CM), alken-alkyn metathesis (en-yn), homometathesis (which is a kind of cross metathesis) and in ring opening metathesis (ROMP).

The products of olefin metathesis reaction obtained using complexes described herein contained low level of residual heavy metal (from about 5 up to about 400 times lower than in the case of product obtained with classical catalysts), and purification process is easy, fast and inexpensive. The simplicity and efficiency of metal containing impurities removal from product is on great importance from industrial (especially pharmaceutical) point of view.

EXAMPLES

Multiplicity abbreviations used when reporting $^1$H NMR spectra are: s—singlet, bs—broad singlet, d—doublet, dd—doublet of doublets, t—triplet, q—quartet, dq—doublet of quartets, sept—septet, pseudot—pseudo triplet.

Example 1

Synthesis of (E/Z)—N-methoxy-N-methylo-2-(2-[prop-1-en-1-yl]phenoxy)propanamid (L1)

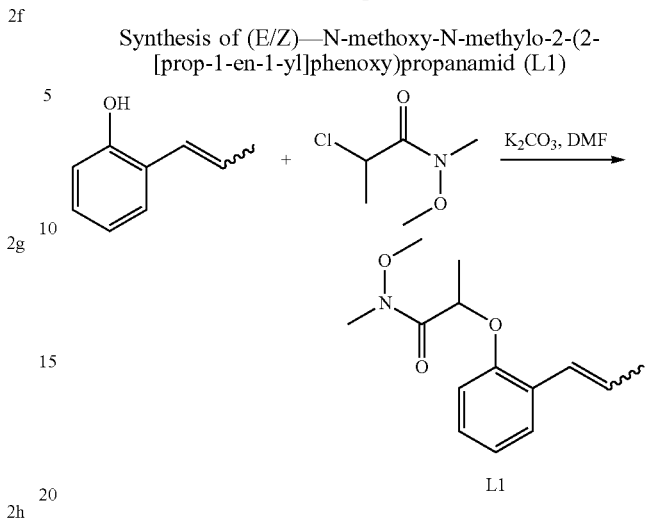

Potassium carbonate (1.63 g, 11.8 mmol) was added to a solution of 2-propenylphenol (0.79 g, 5.9 mmol, mixture of isomers E and Z) in DMF (15 ml) and resulting mixture was stirred at room temperature for 15 min. Next 2-chloro-N-methoxy-N-methylo-propionamid (1.16 g, 7.67 mmol) was added and the reaction mixture was stirred at 50° C. for 24 h. Then DMF was removed and water (30 ml) was added to the residue. The product was extracted with ethyl acetate (3×10 ml). The combined organic fractions were dried with magnesium sulfate. Drying agent was filtered off and solvent was removed. Crude product was purified by vacuum distillation (bp 78-82° C., p=4×10$^{-2}$ mbar) to give L1 (1.30 g, 88%) as yellow oil.

Mixture of E/Z isomers (6/1) was obtained. E isomer, $^1$H NMR (300 MHz, CDCl$_3$) δ ppm: 7.42 (dd, J=7.7, J=1.7 Hz, 1H), 7.30-6.70 (m, 4H), 6.24 (dq, J=15.9, J=6.6 Hz, 1H), 5.15-5.08 (m, 1H), 3.70 (s, 3H), 3.22 (s, 3H), 1.90 (dd, J=6.6, J=1.8 Hz, 3H), 1.60 (d, J=6.7 Hz, 3H).

Example 2

Synthesis of (E/Z)—N-methoxy-N-methylo-2-(2-[prop-1-en-1-yl]fenoxy)acetamid L2

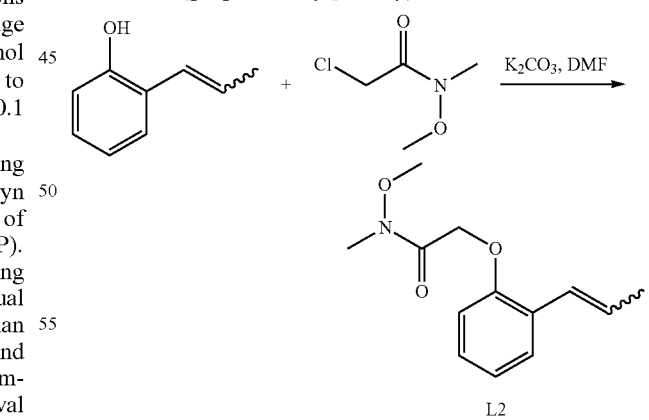

L2 was obtained using procedure described for L1. Yellow oil was obtained with 97% of yield after purification with column chromatography.

Mixture of E/Z isomers (5/1) was obtained. E isomer, $^1$H NMR (300 MHz, CDCl$_3$) δ ppm: 7.45 (dd, J=7.5, J=1.6 Hz, 1H), 7.20-6.80 (m, 4H), 6.30 (dq, J=16.0, J=6.4 Hz, 1H), 4.83 (s, 2H), 3.73 (s, 3H), 3.25 (s, 3H), 1.89 (dd, J=6.7, J=1.7 Hz, 3H).

Example 3

Synthesis of Complex K-1

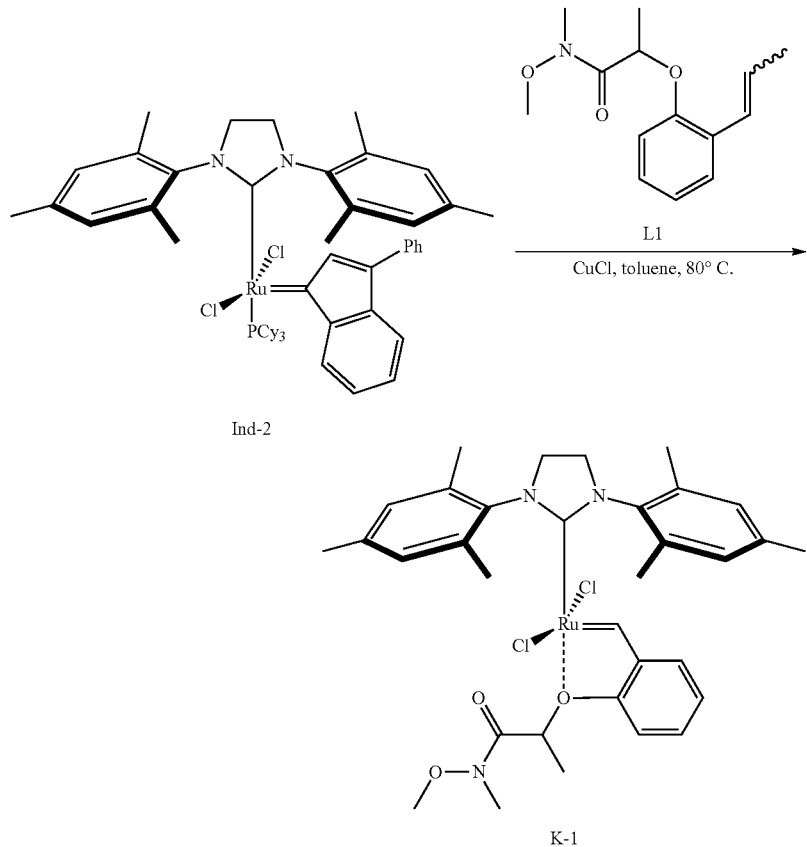

L1 (0.157 g, 0.632 mmol) and copper (I) chloride (0.062 g, 0.632 mmol) were placed under argon in a Schlenk flask and dry, degassed toluene was added (10 ml). Next commercially available complex Ind-2 (0.400 g, 0.421 mmol) was added and reaction mixture was stirred at 80° C. for 20 min. After that reaction mixture was cooled down to room temperature and solvent was removed. The residue was dissolved in minimal amount of ethyl acetate. The insoluble grey solid was filtered off and filtrate was purified using column chromatography (eluent: cyclohexane/ethyl acetate—6/4). Removal of solvents afforded K-1 (0.201 g, 68%) as a green solid.

$^1$H NMR (300 MHz, CDCl$_3$) δ ppm: 16.11 (s, 1H), 7.47-7.44 (m, 1H), 7.09-6.95 (m, 6H), 6.75 (d, J=8.3 Hz, 1H), 5.25-5.22 (m, 1H), 4.06 (s, 4H), 3.68 (s, 3H), 3.09 (s, 3H), 2.51 (s, 12H), 2.41 (s, 6H), 1.52 (d, J=6.5 Hz, 3H).

Example 4

Synthesis of Complex K-2

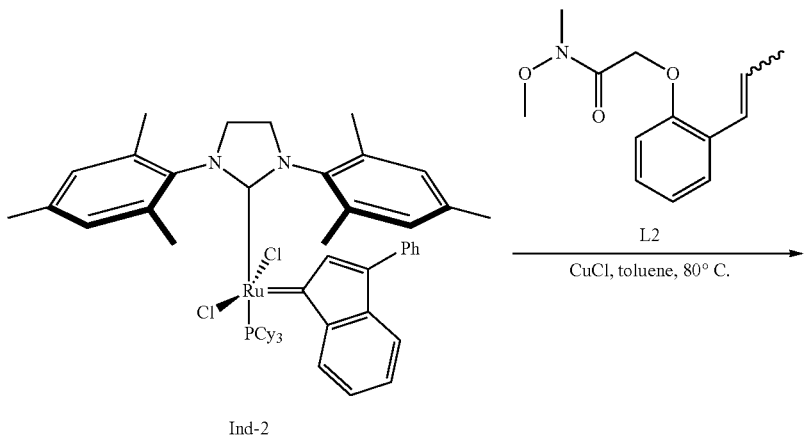

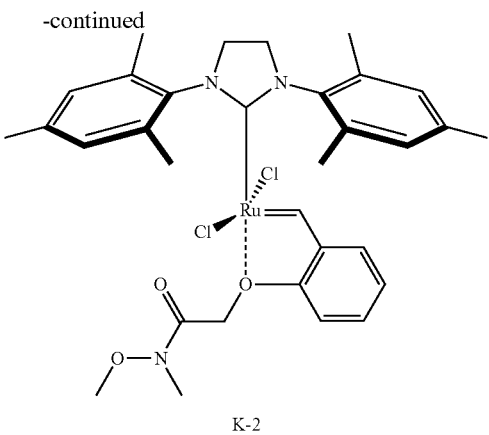

K-2

Complex K-2 was synthesized according to method described for complex K-1. Complex K-2 was obtained as an olive solid in 62% of yield. $^1$H NMR (300 MHz, CDCl$_3$) δ ppm: 15.77 (s, 1H), 7.53-7.47 (m, 1H), 7.09-7.02 (m, 6H), 6.80 (d, J=8.2 Hz, 1H), 4.79 (s, 2H), 4.07 (s, 4H), 3.66 (s, 3H), 3.11 (s, 3H), 2.51 (s, 12H), 2.42 (s, 6H).

Example 5

Synthesis of Complex K-3

$^1$H NMR (300 MHz, CDCl$_3$) δ ppm: 16.46 (s, 1H), 7.60-7.30 (m, 7H), 6.94-6.65 (m, 3H), 5.38-5.17 (m, 1H), 4.13 (s, 4H), 3.70-3.60 (m, 7H), 2.97 (s, 3H), 1.55 (d, J=6.4 Hz, 3H), 1.33-1.12 (d, J=6.8 Hz, 24H). $^{13}$C NMR (75.4 MHz, CDCl$_3$) δ ppm: 297.7, 214.1, 170.6, 151.8, 149.0, 145.9, 138.1, 128.9, 128.1, 124.9, 122.6, 112.5, 72.1, 61.4, 54.6, 32.5, 29.6, 26.4, 23.6, 17.6.

Example 6

Synthesis of Complex K-4

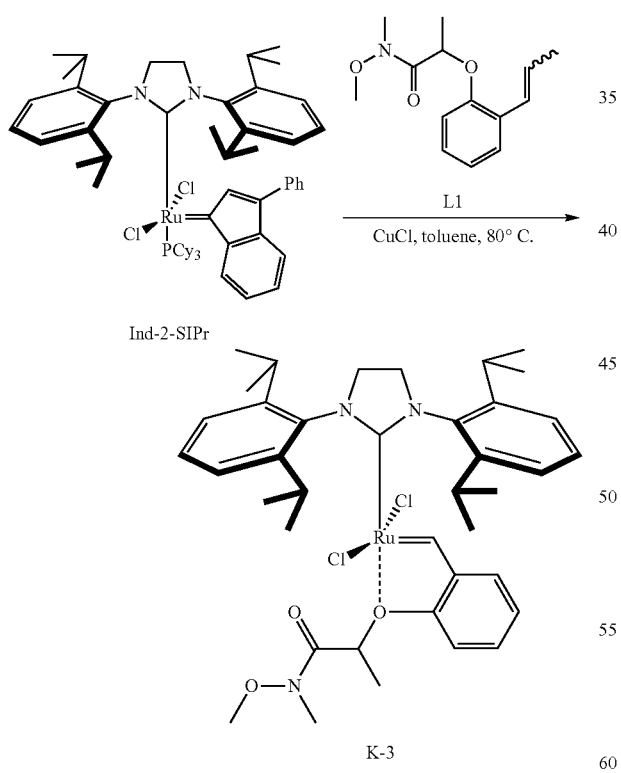

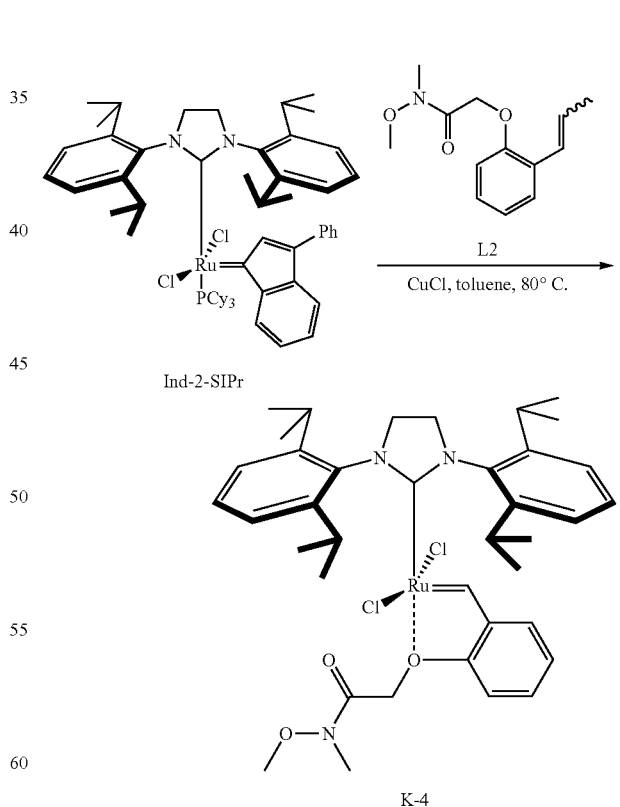

Complex K-3 was synthesized according to method described for complex K-1 with the exception that complex Ind-2-SIPr (H. Clavier, C. A. Urbina-Blanco, S. P. Nolan, Organometallics 2009, 28, 2848-2854) was used as a ruthenium source. Complex K-3 was obtained as a green solid in 72% of yield.

Complex K-4 was synthesized according to method described for complex K-1 with the exception that complex Ind-2-SIPr was used as a ruthenium source. Complex K-3 was obtained as a green solid in 62% of yield.

$^1$H NMR (300 MHz, CDCl$_3$) δ ppm: 16.47 (s, 1H), 7.56-7.44 (m, 3H), 7.42-7.32 (m, 4H), 7.00-6.86 (m, 2H), 6.81 (d, J=8.2 Hz, 1H), 4.83 (s, 2H), 4.14 (s, 4H), 3.63 (s, 7H), 3.04 (s, 3H), 1.31-1.16 (m, 24H). $^{13}$C NMR (75.4 MHz, CDCl$_3$) δ ppm: 298.5, 213.7, 167.8, 153.0, 149.1, 146.2, 138.2, 128.9, 128.1, 124.3, 122.2, 113.3, 65.4, 61.4, 54.6, 32.5, 28.6, 26.5, 23.7.

Example 7

Synthesis of Complex K-5

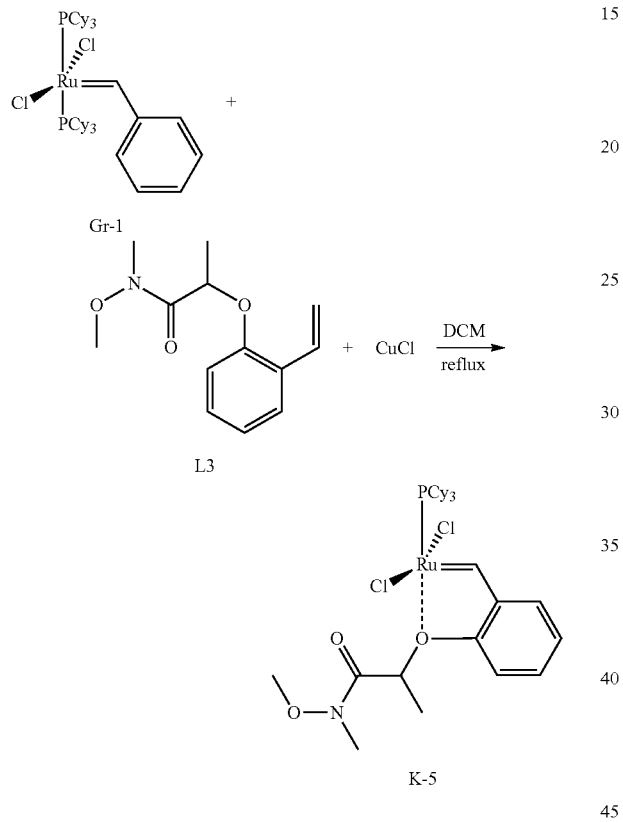

Commercially available complex Gr-1 (0.500 g, 0.61 mmol), L3 (0.161 g, 0.73 mmol) and cooper (I) chloride (0.09 g, 0.91 mmol) were placed under argon in Schlenk flask and dry, degassed dichloromethane (10 ml) was added. The reaction mixture was stirred at 40° C. for 20 min. Then solvent was removed and residue was purified using column chromatography (eluent: c-hexane/ethyl acetate 6/4). Solvents were removed and product was washed with n-pentane to afford K-5 as a green solid in 75% of yield.

Ligand L3 was synthesized according to the method described for L1, except that triphenylmethylphosphonium bromide was used as a Wittig reagent source.

$^1$H NMR (300 MHz, CDCl$_3$) δ ppm: 17.44 (s, 1H), 7.75 (d, J=6.9 Hz, 1H), 7.66 (pseudot, 1H), 7.17 (pseudot, 1H), 7.05 (d, J=6.3 Hz, 1H), 5.60 (q, J=6.0 Hz, 1H), 3.85 (s, 3H), 3.49 (s, 3H), 2.44-2.32 (m, 3H), 2.09-1.81 (m, 24H), 1.33-1.21 (m, 9H). $^{13}$C NMR (75.4 MHz, CDCl$_3$) δ ppm: 290.4, 172.6, 152.8, 147.1, 128.5, 124.6, 123.7, 113.0, 73.4, 61.9, 34.9, 34.6, 32.5, 29.4 (d), 28.1-27.8 (m), 26.9, 26.8, 22.4, 18.2, 14.1. $^{31}$P NMR (121.5 MHz, CDCl$_3$) δ ppm: 57.47 (100%).

Example 8

Synthesis of Complex K-3 from Complex K-5

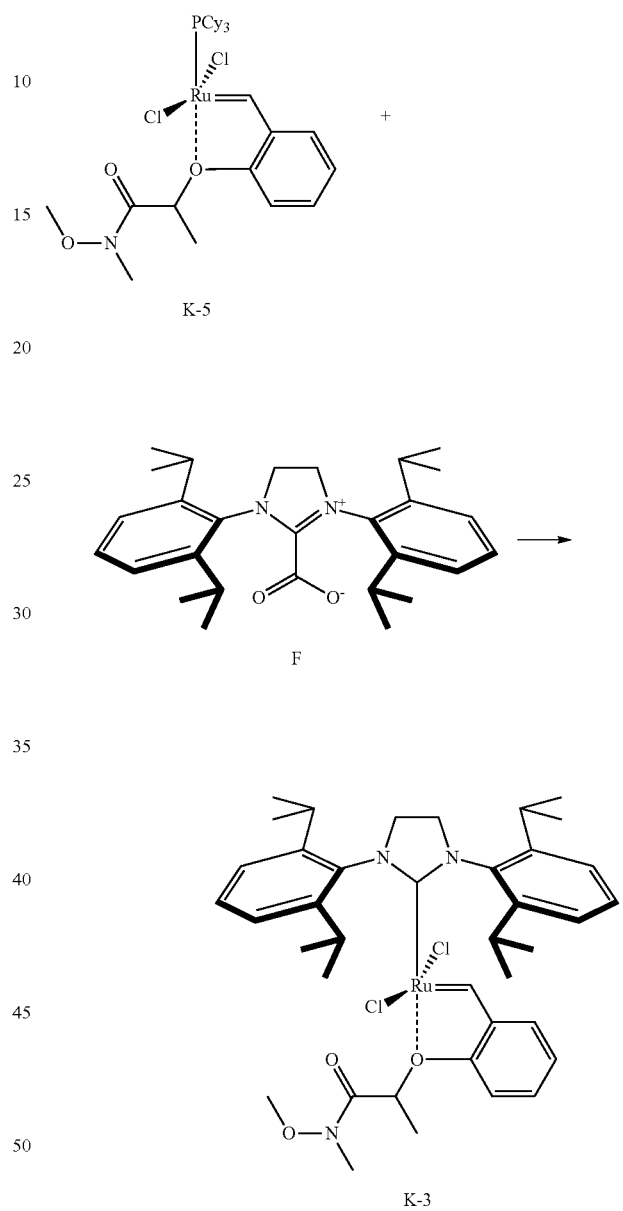

K-5 (0.060 g, 0.09 mmol) and F (0.078 g, 0.18 mmol) was place under argon in the Schlenk flask and dry, degased toluene (2 ml) was added. The reaction mixture was stirred at 80° C. for 1 h. Then solvent was removed and residue was purified using column chromatography (eluent: cyclohexane/ethyl acetate—6/4). Solvents were evaporated to afford K-3 (0.030 g, 43%) as a green solid.

The exact conditions for the examples presented below are given in the tables. Example 9

Comparison of the activity of complexes described herein with complexes known in the literature based on conversions determined by GC.

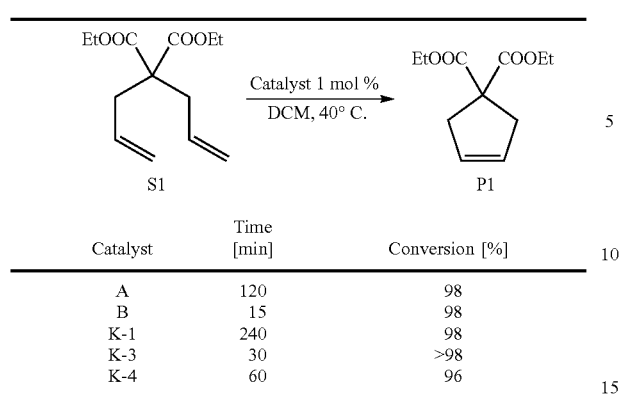

| Catalyst | Time [min] | Conversion [%] |
| --- | --- | --- |
| A | 120 | 98 |
| B | 15 | 98 |
| K-1 | 240 | 98 |
| K-3 | 30 | >98 |
| K-4 | 60 | 96 |

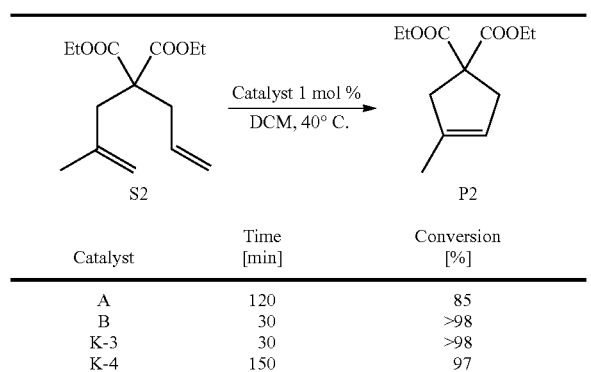

| Catalyst | Time [min] | Conversion [%] |
| --- | --- | --- |
| A | 120 | 85 |
| B | 30 | >98 |
| K-3 | 30 | >98 |
| K-4 | 150 | 97 |

Example 10

Ring Closing Metathesis

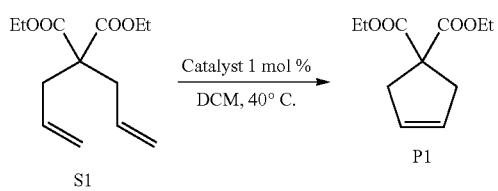

To the solution of S1 (165 mg, 0.69 mmol) in dichloromethane the appropriate amount of catalyst (1 mol %) was added under air. Reaction mixture was stirred at reflux and reaction progress was monitored using GC method. After reaction was completed, reaction mixture was filtered through a short pad of silica gel (silica gel/substrate mas ratio=7). Product was eluted with additional portion of DCM. In each case P1 was isolated with quantitative yield. GC purity of product was determined and residual ruthenium in product was measured using ICP MS method.

| Entry | Catalyst | Time [min] | GC purity [%] | Ru [ppm] |
| --- | --- | --- | --- | --- |
| 1 | B | 30 | 99 | 2180 |
| 2 | K-3 | 30 | 98 | 14 |
| 3 | K-4 | 60 | 93 | 41 |

Example 11

Ring Closing Metathesis

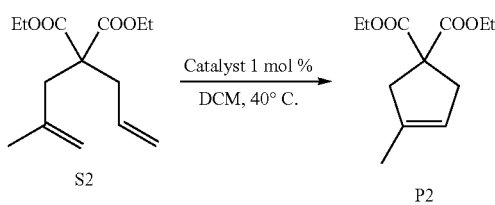

To the solution of S2 (196 mg, 0.77 mmol) in dichloromethane the appropriate amount of catalyst (1 mol %) was added under air. Reaction mixture was stirred at reflux and reaction progress was monitored using GC method. After reaction was completed, reaction mixture was filtered through a short pad of silica gel (silica gel/substrate mas ratio=7). Product was eluted with additional portion of DCM. In each case P2 was isolated with quantitative yield. GC purity of product was determined and residual ruthenium in product was measured using ICP MS method.

| Entry | Catalyst | Time [min] | GC purity [%] | Ru [ppm] |
| --- | --- | --- | --- | --- |
| 1 | A | 120 | 94 | 3640 |
| 2 | A | 120 | 97 | 658[a] |
| 3 | A | 120 | 89 | 293[b] |
| 4 | B | 50 | 98 | 1950 |
| 5 | E | 60 | 94 | 2630 |
| 6 | K-3 | 60 | 96 | 9.2 |
| 7 | K-4 | 150 | 97 | 147 |

[a]residual Ru was removed from crude reaction mixture using commercially available scavenger: SiliaBond Thiol, using procedure recommended by SILICYCLE
[b]residual Ru was removed from crude reaction mixture using commercially available scavenger: SiliaBond DMT, using procedure recommended by SILICYCLE

Example 12

Alkene-Alkyne Metathesis (En-Yn)

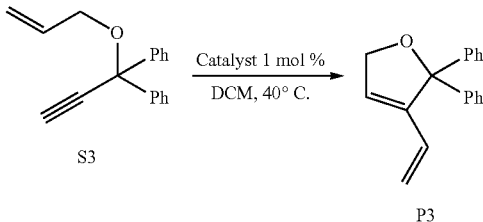

To the solution of S3 (181 mg, 0.73 mmol) in dichloromethane the appropriate amount of catalyst (1 mol %) was added under air. The reaction mixture was stirred at reflux and reaction progress was monitored using GC method. After reaction was completed, reaction mixture was filtered through a short pad of silica gel (silica gel/substrate mas ratio=7). Product was eluted with additional portion of DCM. In each case P3 was isolated with quantitative yield. GC purity of product was determined and residual ruthenium in product was measured using ICP MS method.

| Entry | Catalyst | Time [min] | GC purity [%] | Ru [ppm] |
|---|---|---|---|---|
| 1 | B | 15 | >99.5 | 1430 |
| 2 | K-3 | 30 | >99.5 | 15 |
| 3 | K-4 | 45 | 99 | 37 |

Example 13

Cross Metathesis

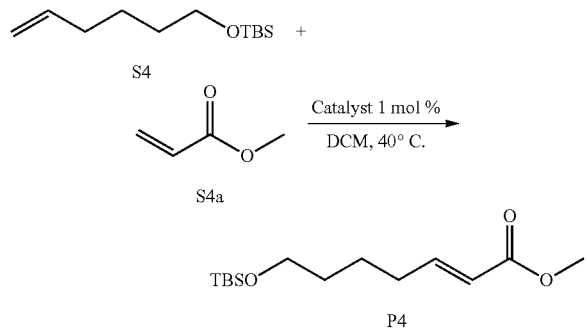

To the solution of S4 (300 mg, 1.40 mmol) and S4a (603 mg, 7.00 mmol) in dichloromethane the appropriate amount of catalyst (1 mol %) was added under air. Reaction mixture was stirred at reflux and reaction progress was monitored using GC method. After reaction was completed, reaction mixture was filtered through a short pad of silica gel (silica gel/substrate mas ratio=7). Product was eluted with additional portion of DCM. GC purity of product was determined and residual ruthenium in product was measured using ICP MS method.

| Entry | Catalyst | Time[min] | GC purity [%] | E/Z | Yield [%] | Ru [ppm] |
|---|---|---|---|---|---|---|
| 1 | A | 40 | 56[c] | 21/1 | 87 | 2550 |
| 2 | A | 40 | 95 | 21/1 | 89 | 1310[a] |
| 3 | A | 40 | 91 | 19/1 | 99 | 109[b] |
| 4 | B | 15 | 99 | 17/1 | 94 | 704 |
| 5 | K-3 | 50 | 96 | 16/1 | 92 | 143 |
| 6 | K-4 | 120 | 97 | 16/1 | 93 | 113 |

[a]-residual Ru was removed from crude reaction mixture using commercially available scavenger: SiliaBond Thiol, using procedure recommended by SILICYCLE
[b]-residual Ru was removed from crude reaction mixture using commercially available scavenger: SiliaBond DMT, using procedure recommended by SILICYCLE
[c]-conversion >98%

Example 14

Ring Closing Metathesis

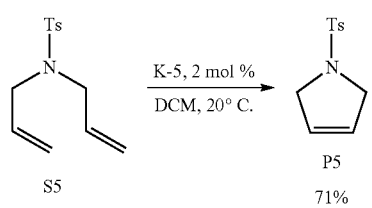

To the solution of S5 (165 mg, 0.69 mmol) in dichloromethane complex K-5 (12.07 mg, 2 mol %) was added. Reaction mixture was stirred at 20° C. and reaction progress was controlled using GC. After reaction was completed, solvent was removed and crude product was crystallized from ethanol twice. Product P5 was obtained as a white solid (145 mg, 71%, GC purity >99%). Residual Ru (61 ppm) was measured using ICP MS method.

Example 15

Catalyst Recovery and Reuse

Example 15 A

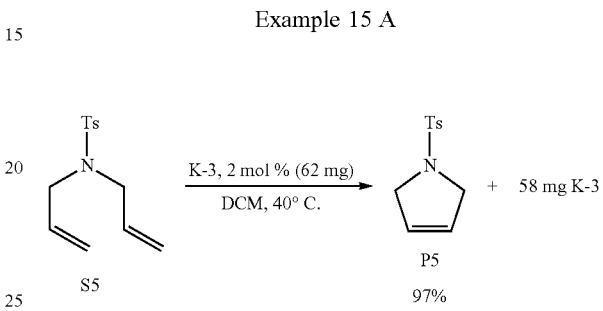

To the solution of S5 (1.0 g, 3.98 mmol) in dry, degased dichloromethane complex K-3 (2 mol %, 62 mg) was added under argon. The reaction mixture was stirred at reflux and reaction progress was monitored using GC method. After reaction was completed (20 min), reaction mixture was filtered through a short pad of silica gel (silica gel/substrate mas ratio=7). Product was eluted with additional portion of DCM. Product was isolated with 97% of yield (862 mg). Purity of product determined by GC was >99%. Residual Ru (48 ppm) in the product was measured by ICP MS method. Next complex K-3 was eluted using ethyl acetate. After solvent removal and catalyst washing with small amount of n-pentane, complex K-3 was recovered as a green solid (56 mg, 90% of initial amount of K-3).

Example 15 B

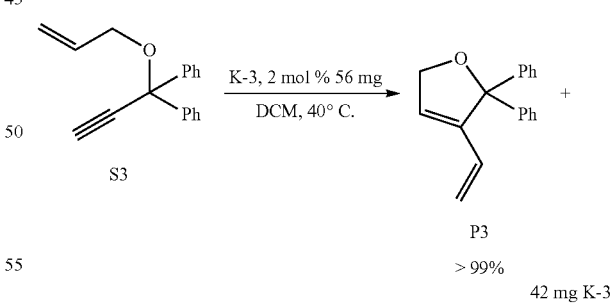

To the solution of S3 (886 mg, 3.57 mmol) in dry, degased dichloromethane complex K-3 (2 mol %, 56 mg) recovered form Example 15A was added under argon. Reaction mixture was stirred at reflux and reaction progress was monitored using GC method. After reaction was completed (30 min), reaction mixture was filtered through a short pad of silica gel (silica gel/substrate mas ratio=7). Product was eluted with additional portion of DCM. Product was isolated with >99% of yield (885 mg). Purity of product determined by GC was >99%. Residual Ru in the product was measured by ICP MS (61 ppm). Next complex K-3 was eluted using ethyl acetate. After solvent removal and catalyst washing with small amount of n-pentane, complex K-3 was recovered as a green solid (42 mg, 75% of the amount of K-3 used in this experiment).

Przyklad 15 C

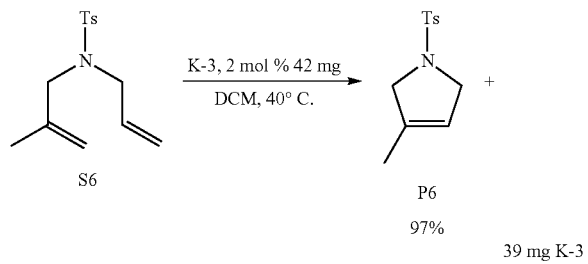

To the solution of S6 (710 mg, 2.68 mmol) in dry, degased dichloromethane complex K-3 (2 mol %, 42 mg) recovered form Example 15B was added under argon. The reaction mixture was stirred at reflux and reaction progress was monitored using GC method. After reaction was completed (30 min), reaction mixture was filtered through a short pad of silica gel (silica gel/substrate mas ratio=7). Product was eluted with additional portion of DCM. Product was isolated with 97% of yield (613 mg). Purity of product determined by GC was >99%. Residual Ru in the product was measured by ICP MS (172 ppm). Next complex K-3 was eluted using ethyl acetate. After solvent removal and catalyst washing with small amount of n-pentane, complex K-3 was recovered as a green solid (39 mg, 93% of the amount of K-3 used in this experiment).

Example 16

Ring Opening Metathesis

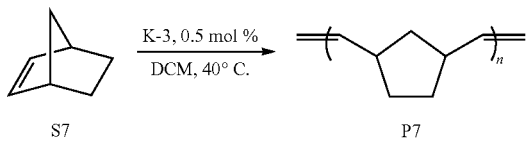

Complex K-3 (12.5 mg, 0.5 mol %) was added to the solution of S7 (300 mg, 3.19 mmol) in dichloromethane (30 ml). The reaction mixture was stirred at 40° C. for 5 min, then cooled down to room temperature and pour out into flask contained methanol (50 ml). Precipitated solid was filtered and dried to afford P7 with 99% of yield (298 mg). Residual Ru in the product was measured by ICP MS (59 ppm).

As it is shown in Example 15 (using complex K-3) complexes described herein have high and selective (dependent on the eluent used) affinity to adsorbents what allow for easy recovery of catalyst after reaction. It is demonstrated that recovered catalyst can be reused maintaining high reactivity and efficiency. Moreover recovered catalyst can be used in metathesis of different substrate giving products of very high purity.

It is demonstrated that complexes described herein such as K-3, K-4 and K-5 (Examples 9-16), can be used as catalyst for olefin metathesis as they shown high efficiency and products obtained using them are contaminated with low residual Ru. Products obtained using classical catalysts contained from 5 up to 400 times more residual ruthenium when the same purification method was applied. Complexes bearing ligand 2d exhibited higher activity and efficiency in metathesis reactions than that containing ligand 2c. Importantly, complexes bearing ligand 2d have activity close to that presented by complex B which is known to be one of the most active metathesis catalyst and usually outweigh in the activity unmodified complex A.

Moreover complexes described herein efficiently mediate metathesis reactions without protective atmosphere of inert gas.

The invention claimed is:

1. A process for carrying out a metathesis reaction, comprising:
preparing a mixture comprising at least one olefin and a catalyst; and
allowing the mixture to react,
wherein the metathesis reaction is ring closing metathesis, ring opening metathesis, cross metathesis, or alkene-alkyne metathesis, and
wherein the catalysis is a compound of a formula:

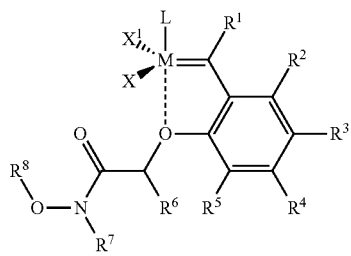

wherein
M is ruthenium;
X and $X^1$ are independently halide, $-OR^9$, $-O(C=O)R^9$, or $-O(SO_2)R^9$, wherein $R^9$ is $C_1$-$C_{12}$ alkyl, $C_3$-$C_{12}$ cycloalkyl, or $C_5$-$C_{14}$ aryl, wherein $R^9$ may be optionally substituted with $C_1$-$C_6$ alkyl, $C_1$-$C_6$ perhaloalkyl, $C_1$-$C_6$ alkoxy, or halide;
L has the formula $P(R^{18})(R^{19})(R^{20})$ or is N-heterocyclic carbene ligand of formulae 2a or 2b:

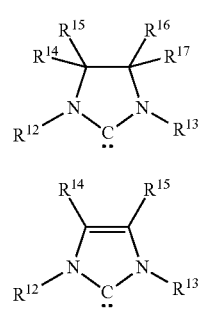

wherein:
$R^1$ is hydrogen, $C_{1-20}$ alkyl, or $C_{5-10}$ aryl;
$R^2$, $R^3$, $R^4$, and $R^5$ are independently hydrogen, halide, $C_{1-20}$ alkyl, $C_{2-20}$ alkenyl, $C_{2-20}$ alkynyl, $C_{5-10}$ aryl, $C_{1-20}$ alkoxy, $C_{2-20}$ alkenyloxy, $C_{2-20}$ alkynyloxy, $C_{5-10}$ aryloxy, $C_{1-20}$ alkoxycarbonyl, $C_{1-20}$ alkylamino, $C_{1-20}$ protonated alkylamino, amino, $C_{1-20}$ protonated amino, $C_{1-20}$ alkylammonium, nitro, carboxy, amido, sulfonamido, or $C_{1-20}$ perhaloalkyl; all those groups except hydrogen and halide can be optionally substituted with $C_{1-20}$ alkyl, $C_{1-20}$ perhaloalkyl, or $C_{5-10}$ aryl;

wherein 2 or more of $R^2$, $R^3$, $R^4$, and $R^5$ may be linked together to form;
  1) a substituted or unsubstituted, fused $C_{4-8}$ carbocyclic ring, or
  2) a substituted or unsubstituted, fused aromatic $C_{5-14}$ ring;

$R^6$, $R^7$, and $R^8$ are independently hydrogen, $C_{1-6}$ alkyl, $C_{4-10}$ cycloalkyl, $C_{4-10}$ heterocyclyl, or $C_{5-14}$ aryl, wherein $R^7$ and $R^8$ may be linked together to form a substituted or unsubstituted $C_{4-8}$ cyclic system;

$R^{12}$ and $R^{13}$ are independently $C_5$-$C_{14}$ aryl, optionally substituted with $C_1$-$C_{12}$ alkyl, $C_1$-$C_{12}$ perhaloalkyl, $C_1$-$C_{12}$ alkoxy, or halide;

$R^{14}$, $R^{15}$, $R^{16}$, and $R^{17}$ are independently hydrogen or $C_1$-$C_{12}$ alkyl; and $R^{18}$, $R^{19}$ and $R^{20}$ are independently $C_{1-12}$ alkyl, $C_{1-12}$ alkoxy, $C_{3-12}$ cycloalkyl, $C_{5-12}$ aryl, $C_{5-12}$ aryloxy, or $C_{5-12}$ heterocyclic, wherein two substituents among $R^{18}$, $R^{19}$ and $R^{20}$ may optionally be linked together to form a cyclic system.

2. A process according to claim 1, wherein the metathesis reaction is carried out in organic solvent.

3. A process according to claim 1, wherein any metal impurities resulting from the metathesis reaction are removed from product by filtration of reaction mixture through a pad of appropriate adsorbent.

4. A process according to claim 1, wherein any metal impurities resulting from the metathesis reaction are removed from reaction mixture by addition of an adsorbent to the reaction mixture and filtration.

5. A process according to claim 1 wherein the adsorbent is: silica gel, aluminium oxide, activated aluminium oxide, diatomite, or activated carbon.

6. A process according to claim 5, wherein the adsorbent is silica gel.

7. A process according to claim 1 wherein any metal impurities resulting from the metathesis reaction are removed from product by crystallization from polar solvent.

8. The process according to claim 1, wherein $R^6$, $R^7$, and $R^8$ are independently hydrogen or methyl.

9. The process according to claim 1, wherein
L is N-heterocyclic carbene ligand; and
$R^1$ is hydrogen or $C_{1-20}$ alkyl.

10. The process according to claim 9, wherein $R^6$, $R^7$, and $R^8$ are independently hydrogen or methyl.

11. The process according to claim 1, wherein
L has the formula $P(R^{18})(R^{19})(R^{20})$; and
$R^1$ is hydrogen or $C_{1-20}$ alkyl.

12. The process according to claim 11, wherein $R^6$, $R^7$, and $R^8$ are independently hydrogen or methyl.

13. The process according to claim 1, wherein
X and $X^1$ are independently halide;
L is N-heterocyclic carbene ligand of formulae 2a or 2b:

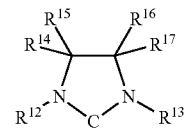

2a

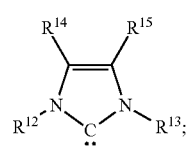

2b and
$R^1$ is hydrogen.

14. The process according to claim 13, wherein $R^6$, $R^7$, and $R^8$ are independently hydrogen or methyl.

15. The process according to claim 1, wherein
X and $X^1$ are chloride;
L is N-heterocyclic carbene ligand of formulae 2c or 2d:

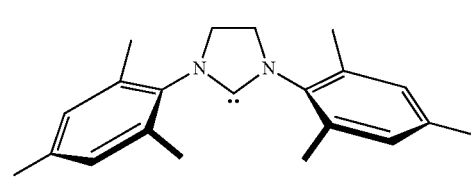

2c

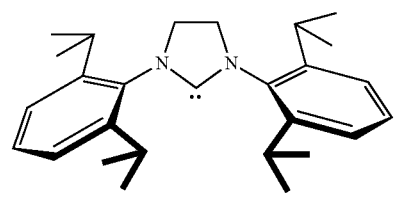

2d $R^1$ is hydrogen;
$R^2$, $R^3$, $R^4$, and $R^5$ are independently hydrogen or nitro;
$R^6$, $R^7$, and $R^8$ are independently hydrogen, $C_{1-6}$ alkyl, or $C_{5-14}$ aryl;
wherein $R^7$ and $R^8$ may be linked together to form a substituted or unsubstituted $C_{4-8}$ cyclic system.

16. The process according to claim 15, wherein $R^6$, $R^7$, and $R^8$ are independently hydrogen or methyl.

17. The process according to claim 1, wherein the mixture comprises:
the catalyst; and
two compounds each having a C=C double bond, or one compound having at least two C=C double bonds.

18. The process according to claim 17 in which the catalyst is used in ring opening metathesis polymerization.

* * * * *